(12) United States Patent
Apker

(10) Patent No.: US 10,871,497 B2
(45) Date of Patent: Dec. 22, 2020

(54) PREDICTING REAGENT CHILLER INSTABILITY AND FLOW CELL HEATER FAILURE IN SEQUENCING SYSTEMS

(71) Applicant: Illumina, Inc., San Diego, CA (US)

(72) Inventor: Gregory Apker, San Diego, CA (US)

(73) Assignee: Illumina, Inc., San Diego, CA (US)

(*) Notice: Subject to any disclaimer, the term of this patent is extended or adjusted under 35 U.S.C. 154(b) by 169 days.

(21) Appl. No.: 16/239,342

(22) Filed: Jan. 3, 2019

(65) Prior Publication Data
US 2019/0212352 A1 Jul. 11, 2019

Related U.S. Application Data

(60) Provisional application No. 62/613,910, filed on Jan. 5, 2018.

(51) Int. Cl.
*G01N 35/00* (2006.01)
*C12Q 1/6869* (2018.01)
*G08B 21/18* (2006.01)

(52) U.S. Cl.
CPC ..... *G01N 35/00623* (2013.01); *C12Q 1/6869* (2013.01); *G08B 21/182* (2013.01); *G08B 21/187* (2013.01)

(58) Field of Classification Search
CPC ............ G01N 35/00623; C12Q 1/6869; C12Q 2535/122; G08B 21/187
See application file for complete search history.

(56) References Cited

U.S. PATENT DOCUMENTS 4,903,192 A * 2/1990 Saito .................. G05B 13/0275
 700/37
5,548,252 A * 8/1996 Watanabe ............... H03L 1/025
 331/116 FE (Continued)

FOREIGN PATENT DOCUMENTS

WO 2015084985 A2 6/2015
WO 2018165099 A1 9/2018

OTHER PUBLICATIONS

"Phasing and Prephasing FAQ", Scientific Knowledge Base, Nov. 29, 2017, 1-20.

(Continued)

*Primary Examiner* — Kun Kai Ma
(74) *Attorney, Agent, or Firm* — Haynes Beffel & Wolfeld, LLP; Ernest J. Beffel, Jr.; Sikander Khan

(57) ABSTRACT

The technology disclosed detects chiller system instability that reduces false alerts. A smoothed time series of chiller temperature sensor data is tested in a predefined time window for periods of stable operation below a predetermined threshold. The technology disclosed predicts that the reagent chiller is unstable if periods of stable temperature operation are less than a predetermined stability measure or if the stable reagent chiller temperature has exceeded a threshold. The technology disclosed detects flow cell heater failure over multiple cycles in a system. A time series of flow cell heater temperature sensor data is tested to determine if a count of points in a recent process cycle were recorded above a threshold. The technology disclosed determines that a flow cell heater is failing if count of points above a threshold in two consecutive cycles is less than a predetermined count.

25 Claims, 8 Drawing Sheets
(3 of 8 Drawing Sheet(s) Filed in Color)

(56) References Cited

U.S. PATENT DOCUMENTS

| | | | |
|---|---|---|---|
| 6,951,998 | B2 | 10/2005 | Nanno et al. |
| 7,669,777 | B2 | 3/2010 | Hull |
| 8,392,126 | B2 | 3/2013 | Mann et al. |
| 8,965,076 | B2 | 2/2015 | Garcia et al. |
| 9,444,880 | B2 | 9/2016 | Dickinson et al. |
| 2008/0088857 | A1* | 4/2008 | Zimmer .............. H04N 1/56 358/1.6 |
| 2010/0157086 | A1 | 6/2010 | Segale et al. |
| 2014/0214579 | A1 | 7/2014 | Shen et al. |
| 2015/0125053 | A1 | 5/2015 | Vieceli |
| 2018/0195953 | A1 | 7/2018 | Langlois et al. |
| 2018/0274023 | A1* | 9/2018 | Belitz .............. C12Q 1/6869 |

OTHER PUBLICATIONS

Hedegaard, J., "An introduction to "Next Generation" DNA Sequencing", AARHUS Universitet http://staff.vbi.vt.edu/mlawre04/NextGen%20Genomics%20Class/Technology%20-%20Module_6_NGS_intro.pdf, 2010, 1-63.

Illumina, "Illumina Two-Channel SBS Sequencing Technology", https://www.illumina.com/science/technology/next-generation-sequencing/sequencing-technology/2-channel-sbs.html, Jan. 4, 2016, 1-2.

Illumina, "Low-Diversity Sequencing on the Illumina HiSeq Platform", https://www.illumina.com/documents/products/technotes/technote-hiseq-low-diversity.pdf, Aug. 20, 2014, 1-2.

Illumina, "Quality Scores for Next-Generation Sequencing", https://www.illumina.com/documents/products/technotes/technote_Q-Scores.pdf, 2011, 1-2.

Illumina, "Reducing Whole-Genome Data Storage Footprint", http://www.illumina.com/documents/products/whitepapers/whitepaper_datacompression.pdf, Apr. 17, 2014, 1-4.

Illumina, "Sequencing Analysis Viewer Software User Guide", https://support.illumina.com/downloads/sequencing-analysis-viewer-software.html, Oct. 17, 2014, 1/33.

Ioffe, S., et al., "Batch Normalization: Accelerating Deep Network Training by Reducing Internal Covariate Shift", arXiv:1502.03167 [cs.LG], Feb. 11, 2015.

Leshkowitz, D., "Illumina Primary Analysis Pipeline and Quality Control", Weizmann Institute of Science, 2016, 1-48.

Townley, D., "Illumina Primary and Secondary Analysis", https://www.illumina.com/documents/seminars/presentations/2010-06_sq_04_townley_ngs_analysis_pdf, Jun. 2010, 1-33.

* cited by examiner

PREDICTING REAGENT CHILLER INSTABILITY AND FLOW CELL HEATER FAILURE IN SEQUENCING SYSTEMS

PRIORITY APPLICATION

This application claims the benefit of U.S. Provisional application No. 62/613,910 filed Jan. 5, 2018, entitled PREDICTING REAGENT CHILLER INSTABILITY AND FLOW CELL HEATER FAILURE IN SEQUENCING SYSTEMS by inventor Gregory Apker. The priority provisional application is hereby incorporated by reference.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also correspond to implementations of the claimed technology.

The technology disclosed relates to sequencing systems including systems applying sequencing-by-synthesis technique for sequencing nucleotides. A sequencing run to identify nucleotides in molecules is an extended process taking multiple days to complete. All subsystems of a sequencing machine need to operate without errors in order for resulting base calls to be useful for downstream analytics. A difficult problem arises to predict consequential malfunctions in operation of sequencing machines before and during a sequencing run. Sensors in sequencing system produce readings that are used to control operating conditions of various components. These readings are used in control loops to alter the future state of the system, but are not available to operators. Even if the sensor readings were available to operators, the problem of predicting consequential malfunctions of sequencing machines would not be adequately addressed, because appropriate sensor values are not self-apparent to an operator.

The subsystems of a sequencing machine can be impacted by external factors including the environment in which they are operating. The sensor readings do not identify whether an unusual sensor reading is due to an unstable or failing subsystem or an external factor. The impact of external factors is usually temporary and the subsystem performance returns to normal level when the external factor is removed. It is desirable to provide a solution to identify whether an out of bounds sensor reading is due to an unstable or failing subsystem or due to an external factor.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The color drawings also may be available in PAIR via the Supplemental Content tab. The included drawings are for illustrative purposes and serve only to provide examples of possible structures and process operations for one or more implementations of this disclosure. These drawings in no way limit any changes in form and detail that may be made by one skilled in the art without departing from the spirit and scope of this disclosure. A more complete understanding of the subject matter may be derived by referring to the detailed description and claims when considered in conjunction with the following figures, wherein like reference numbers refer to similar elements throughout the figures.

DETAILED DESCRIPTION

Figure 1:
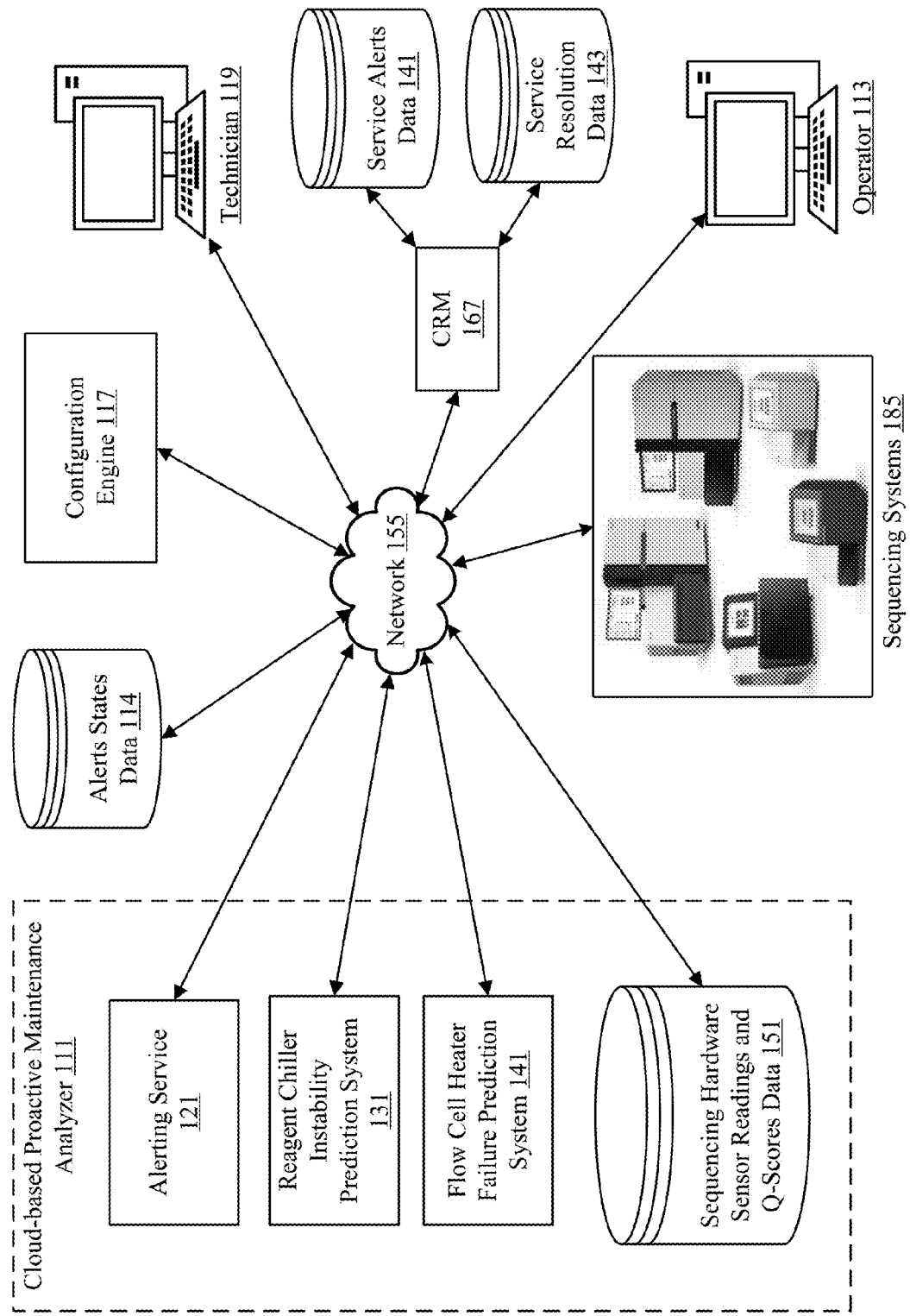
FIG. 1 shows an architectural level schematic of a system in which a reagent chiller instability prediction system predicts chiller system instability and a flow cell heater failure prediction system detects flow cell heater failure, both determined from newly collected sequencing hardware sensor metrics from sequencing systems.

The following detailed description is made with reference to the figures. Sample implementations are described to illustrate the technology disclosed, not to limit its scope, which is defined by the claims. Those of ordinary skill in the art will recognize a variety of equivalent variations on the description that follows.

INTRODUCTION

Sequencing-by-synthesis (SBS) is one of several popular techniques for sequencing nucleotides in a DNA or RNA molecule. The machines that perform sequencing are complex systems comprising sophisticated subsystems operating at specific temperatures during sequencing process steps. The cost to acquire and operate sequencing machines is high. During the sequencing process, the subsystems of a sequencing machine can be impacted by internal and external instabilities.

In SBS process cycles, complementary nucleotides are added one at a time, to a nucleotide sequence fragment (also called as a molecule or an insert) from the DNA to be sequenced. Sequencing nucleotides in molecules proceeds in hundreds of cycles. Before the sequencing cycles begin, a library of molecules to be sequenced is prepared on a slide or a flow cell. The molecules are arranged in tiles within multiple lanes on a flow cell. A cycle includes chemical, image capture and image processing actions. Subsystems, including optical, mechanical, and chemical subsystems, operate in each cycle to identify the complementary nucleotide attached to molecules. Identifying added nucleotides is massively parallel as there are millions or billions of clusters of molecules on a flow cell. A sequencing run includes hundreds of sequencing process cycles and can take multiple days to complete. Sometimes, results of an entire sequencing run are discarded because they do not meet the minimum quality requirements for downstream analysis. Therefore, it is desired to predict a subsystem failure as early as possible if it impacts quality of sequencing results.

The technology disclosed involves modifying sequencers to expose selected data from sensors used by internal control loops, which was not previously collected or analyzed. Selection of sensor data to expose and collect required careful analysis of subsystems and sensors used in control loops.

Development of this technology included analysis of the newly collected sensor data and identification of features in time series data that can be used to predict malfunctions.

Enablement of collection of selected sensor data from many machines in varying environments with different classes of users will support refinement of predictive methods. Analysis of a variety of data should allow the development team to reduce false alerts that undermine confidence in predictions, without missing significant events.

Sensor data collection and analysis during sequencing runs will enable an operator to abort a sequencing run that is likely to fail or to schedule preventative maintenance between runs.

Significantly, predetermined detection parameters and filters are designed to differentiate between error conditions and momentary, transient fluctuations due to external factors, so that false alerts do not cause runs, which should succeed, to be cancelled. For example, a reagent chiller subsystem maintains precise temperature of reagents for a sequencing run. If the door of the room in which the sequencing machine is operating is opened during summer weather, warm air from outside increases the room temperature. When this air enters the reagent chiller compartment, the sensor registers a higher than usual temperature reading. This transient fluctuation should not produce an error condition alert. In this example, an unstable or underperforming reagent chiller system produces an alert after filtering out transient fluctuations in temperatures due to external factors. In another example, the technology disclosed alerts an operator to failure of a flow cell heater, using temperature data form multiple sequencing cycles. A flow cell heater that is warming too slowly can be detected from temperature sensor data, in view of cycle set points or derived thresholds. Failure of the flow cell heater to heat as expected can indicate a failing heater and/or lead to a potentially unsuccessful run.

Analysis of the newly collected sensor data during sequencing enables generation of alarms and alerts to predicted failures of subsystems and sequencing runs that are likely to fail. This should reduce downtime and improve customer satisfaction.

ENVIRONMENT

We describe a system for early prediction of reagent chiller failure and flow cell heater failure in sequencing systems, applied to an extended optical base calling process. Four types of nucleotides in a DNA molecule are Adenine (A), Cytosine (C), Guanine (G), and Thymine (T). Base calling refers to determining a nucleotide base (A, C, G, T) per cluster added to molecules in one cycle of the sequencing run. The system is described with reference to FIG. 1 showing an architectural level schematic of a system in accordance with an implementation. Because FIG. 1 is an architectural diagram, certain details are intentionally omitted to improve the clarity of the description. The discussion of FIG. 1 is organized as follows. First, the elements of the figures are described, followed by their interconnection. Then, the use of the elements in the system is described in greater detail.

FIG. 1 includes the system 100. This paragraph names the labelled parts of system 100. The figure illustrates sequencing systems (or sequencers) 185, operators 113 of sequencing systems, technicians 119, a customer relationship management (CRM) system 167, a service alerts database 141, an alerts states database 114 and a service resolution database 143. The system 100 also includes a sequencing hardware sensor readings and Q-scores database 151, a configuration engine 117, and an alerting service 121. These components contribute to a reagent chiller instability prediction system 131 and a flow cell heater failure prediction system 141. The database 151, alerting service 121, reagent chiller instability prediction system 131, flow cell heater failure prediction system 141 can be implemented as a cloud-based proactive maintenance analyzer 111.

The technology disclosed applies to a variety of sequencing systems 185, also referred to as sequencing instruments and sequencing platforms. The network(s) 155, couples the sequencing systems 185, the operators 113, the CRM system 167, the technicians 119, the configuration engine 117, the alerts states database 114, the alerting service 121, the reagent chiller instability prediction system 131, the flow cell heater failure prediction system 141, and database 151, in communication with one another. The CRM system 167 communicates with the service alerts database 141 and the service resolution database 143 to send alerts to operators 113 and technicians 119. The resolutions of the alerts after service by technicians are stored in service resolution database 143. The CRM system 167 can also be packaged in a customer relations module.

The sequencing systems 185 can use Illumina's sequencing-by-synthesis (SBS) technique or another sequencing technique. Illumina Inc., a manufacturer of sequencing systems 185, offers a variety of sequencing systems including but not limited to, HISEQX™, HISEQ2500™, HISEQ3000™, HISEQ4000™, NOVASEQ6000™, and MISEQDX™. These sequencing machines include a control computer, a monitor and main subsystems containing the flow cells, fluidics and reagents, optics and image capture and processing modules. These sequencing systems apply SBS techniques for base calling cycles in a sequencing run. The sequencing systems 185 are used in a wide variety of physical environments ranging from laboratories in large research facilities to high school class rooms. Many sources of signal noise impact sequencing machines operated in diverse environments. The sequencing machines operators have a wide variety of skill levels, ranging from trained researchers in research laboratories to high school teachers and students using equipment on loan. Some models of sequencing machines are not highly insulated and are thus potentially impacted by weather conditions and by opening of doors and windows.

A sequencing run proceeds over hundreds of process cycles, ranging, for example, from 200 to 600 cycles or 300 to 1000 cycles. Depending on the platform, a sequencing run of 300 cycles can take up to three days to complete. Sometimes, a run is divided into two reads, also referred to as paired-end runs. A cycle includes chemical, image capture and image processing steps. During chemical processing, a complimentary nucleotide is added to each molecule in clusters of molecules arranged in lanes on flow cells. Some subsystems are described in the following paragraphs.

A fluidics subsystem contains fluidics pumps that deliver reagents to the flow cells and then to the waste container. A reagent is a compound or a substance added to the flow cells in the chemical process. Racks in a reagent subsystem hold reagents in sufficient quantity for the entire sequencing run. A reagent chiller houses the reagent racks and maintains the internal temperature near a range of 4 degrees C. It is understood that in other sequencing systems, a reagent chiller can maintain a different temperature range.

A flow cell subsystem can include a flow cell stage, which holds the flow cell in place during sequencing runs. Some stages hold two flow cells. Heaters ramp up the flow cells to suitable reaction temperatures during a sequencing cycle.

The optics subsystem includes optical components that enable imaging of the flow cells to identify A, C, G, and T bases using fluorescently tagged complimentary nucleotides. Excitation laser beam excites the fluorescent tags. Cameras are used to capture images that are processed to call bases. In other embodiments of sequencers, CMOS sensors overlaid by nanowells have been used as a base for a flow cell, replacing overhead cameras.

Sequencing systems and subsystems use many sensors in control loops. System software has been updated to log selected sensor readings that previously were used only for internal control loops. Sequencing systems can be retrofitted (or initially configured), for example by deployment of a software patch, so that a sensor reading, which was previously only used for internal control, will be collected and/or logged. The collected sensor readings can be sent to the cloud-based data proactive maintenance analyzer 111 or stored locally to the sequencer or within an enterprise network.

In one implementation, the cloud-based proactive maintenance analyzer 111 aggregates collected sensors readings. The platform directly integrates with sequencing machines offered. Instrument operations data can be sent from sequencing systems 185 to cloud-based proactive maintenance analyzer 111 via the network 155. In another implementation, a local version of the cloud-based proactive maintenance analyzer 111 enables data storage and analysis onsite through an installed local server. Operations data for a particular sequencing run from a sequencing machine is stored as a data set of time series data. The operations data can be stored a time series of quality data, such as Q-scores for cycles and other metrics including intensity and phasing/prephasing. The quality data can be used as a dependent variable in analysis of independent sensor readings.

Data collected can be used to establish or to update predetermined detection parameters and filters. For instance, the cloud-based proactive maintenance analyzer collects and analyzes the time series and quality data to set or update the predetermined detection parameters. The proactive maintenance analyzer also can update the predetermined detection parameters periodically, combining collected time series data with service resolution data that separates correct from false alerts and indicates how an alert was resolved. Time series data from equipment that failed without warning also can be taken into account when updating the predetermined detection parameters. Both missed failures and false alerts can be identified using the service resolution data from the CRM system and used to refine the predetermined detection parameters and corresponding time series filtering.

The sequencing systems 185 report the sensor readings during or following the sequencing process. They also report quality-related data. Collections of sensor and/or quality readings can be referred to as logs. The collected sensor readings and quality data are stored in database 151, the sequencing hardware sensor readings and Q-score database 151. The database 151 can store time series of sensor readings organized according to base calling cycles per sequencing system. The database 151 can also store quality scores of the base calling cycles per sequencing system as a dependent variable. A Q-score is a commonly used quality score predicting the probability of an error in base calling. Details of Q-score are presented in a technical note Quality Scores for Next Generation Sequencing (2011)<accessed at https://www.illumina.com/documents/products/technotes/technote_Q-Scores.pdf on Dec. 6, 2018>. A high Q-score indicates that a base call is more reliable and less likely to be incorrect. In one implementation, database 151 stores reagent chiller temperature and flow cell heater temperature reported by sensors.

Several examples of quality metrics in addition to Q-scores follow. For example, the chemical processing subsystem generates phasing and prephasing metrics. The term "phasing" describes a situation when a molecule in a cluster of molecules falls at least one base behind other molecules in the same cluster during sequencing process. This result may be due to an incomplete chemical reaction. The term "prephasing" describes a situation in which a molecule jumps at least one base ahead of other molecules in the same cluster of molecules. One reason for prephasing is the incorporation of an unterminated nucleotide, and subsequent incorporation of a second nucleotide in the same sequencing cycle. Increased phasing or prephasing detracts from accuracy of calling by confusing the luminescent signal from a cluster. Thus, phasing and prephasing measures can be used with sensor time series data to set or update the predetermined detection parameters.

The optics subsystem produces intensity measures that can be used as quality data. Some sequencers use cameras to capture images of clusters on flow cells during a sequencing cycle. The image acquisition includes intensity measures for cycles in a sequencing run. The process of determining an intensity value for a cluster in a sequencing image is referred to as intensity extraction. To extract intensity, a background is computed for a cluster of molecules using a portion of the image containing the cluster. The signal for the background is subtracted from the signal for the cluster to determine the intensity. The sequencing hardware sensor readings and Q-scores database 151 can store one or more imaging performance metrics as dependent variables.

The configuration engine 117 can be used to deliver software patches that retrofit the sequencing system and expose sensor readings for collection and logging. The newly collected sensor reading data is analyzed to determine the predetermined detection parameters for the sensor readings of different sequencing system components or subsystems. After the predetermined detection parameters are determined, the sensor readings from the sequencing systems are tested against these predetermined detection parameters to predict consequential subsystem malfunctions. Further details of the configuration engine 117 and alerting service 121 are presented in the description of subsystem components illustrated in FIG. 2. The reagent chiller subsystem and flow cell heater subsystem are two example subsystems of sequencing systems which have been retrofitted by the technology disclosed to collect sensor readings.

The reagent chiller system refrigerates reagents stored in racks within a housing to a cold temperature, such as around 4 degree Celsius for one type of chemical process. Reagents used in the sequencing systems are chilled until used in the chemical process. Failure of the reagent chiller to compensate for fluctuations in ambient temperature can spoil reagents by exposing stored reagents to a higher than desired temperature for an extended period of time. The reagent chiller instability prediction system 131 uses reagent chiller temperature data reported by a temperature sensor in reagent chiller to identify instabilities in operation of reagent chiller. In one implementation, software reports readings from the sensors in the reagent chiller at five-minute intervals. It is understood that in other implementations, the temperature sensor data can be reported at time intervals greater or less than five minutes, such as in a range of 1 to 30 minutes or 30 seconds to an hour. The data reported by the temperature sensor in reagent chiller can be noisy due to mechanical systems used in the operation of the chiller subsystem. The temperature of the chiller subsystem is impacted by external factors, such as the environment in which the sequencing machine is operating, and by operation of the reagent chiller subsystem. The reagent chiller instability prediction system 131 analyzes the time series of chiller temperature sensor data to determine whether the reagent chiller system is unstable. More details are presented in the description of subsystem components in FIG. 2.

Flow cell heaters and chillers, respectively, heat and chill flow cells and reagents to temperatures required for the chemical processes that attach and remove florescent tags, which are imaged and translated into base calls. The chemical processes proceed at different temperatures. In one sequencing cycle implementation, the flow cell temperature is ramped up from an initial value of 20° C. to 55° C. for a brief moment and then to 60° C. for another brief moment of time. Before imaging, the temperature of the flow cell drops back to 20° C. The temperature ramp-up and cool-down is repeated in the next sequencing cycle. Flow cell heater failure prediction system 141 analyzes the time series of flow cell heater temperature sensor data to determine if the flow cell heater has failed. The details of reagent chiller instability prediction system 131 and flow cell heater failure prediction system 141 are presented in the description of subsystem components in FIG. 2.

When the failure prediction systems, such as the reagent chiller instability prediction system 131 and flow cell heater failure prediction system 141, indicate approaching hardware failure, the alerting service 121 generates service alerts. The CRM system 167 relays alerts that enable operators 113 and/or technicians 119 to set up service calls for servicing the sequencing systems 185. The alerts are stored in service alerts database 141. The states of the alerts are maintained in the alerts state database 114 to manage escalation of service requests in a planned manner, for example, according to service level agreements. The service resolution database 143 includes details of the equipment service performed by the technician. Missed failures and false alerts can be used for the purpose of adjusting the predetermined detection parameters. Missed failures can be used as false negatives and false alerts can be used as false positives. For example, in flow cell heater failure prediction, false positives can indicate that the threshold above the ambient temperature may need to be increased. For false negatives, the threshold may need to be decreased.

Completing the description of FIG. 1, the components of the system 100, described above, are all coupled in communication the network(s) 123. The actual communication path can be point-to-point over public and/or private networks. The communications can occur over a variety of networks, e.g., private networks, VPN, MPLS circuit, or Internet, and can use appropriate application programming interfaces (APIs) and data interchange formats, e.g., Representational State Transfer (REST), JavaScript Object Notation (JSON), Extensible Markup Language (XML), Simple Object Access Protocol (SOAP), Java Message Service (JMS), and/or Java Platform Module System. All of the communications can be encrypted. The communication is generally over a network such as the LAN (local area network), WAN (wide area network), telephone network (Public Switched Telephone Network (PSTN), Session Initiation Protocol (SIP), wireless network, point-to-point network, star network, token ring network, hub network, Internet, inclusive of the mobile Internet, via protocols such as EDGE, 3G, 4G LTE, Wi-Fi and WiMAX. The engines or system components of FIG. 1 are implemented by software running on varying types of computing devices. Example devices are a workstation, a server, a computing cluster, a blade server, and a server farm. Additionally, a variety of authorization and authentication techniques, such as username/password, Open Authorization (OAuth), Kerberos, SecureID, digital certificates and more, can be used to secure the communications.

SYSTEM COMPONENTS

Figure 2:
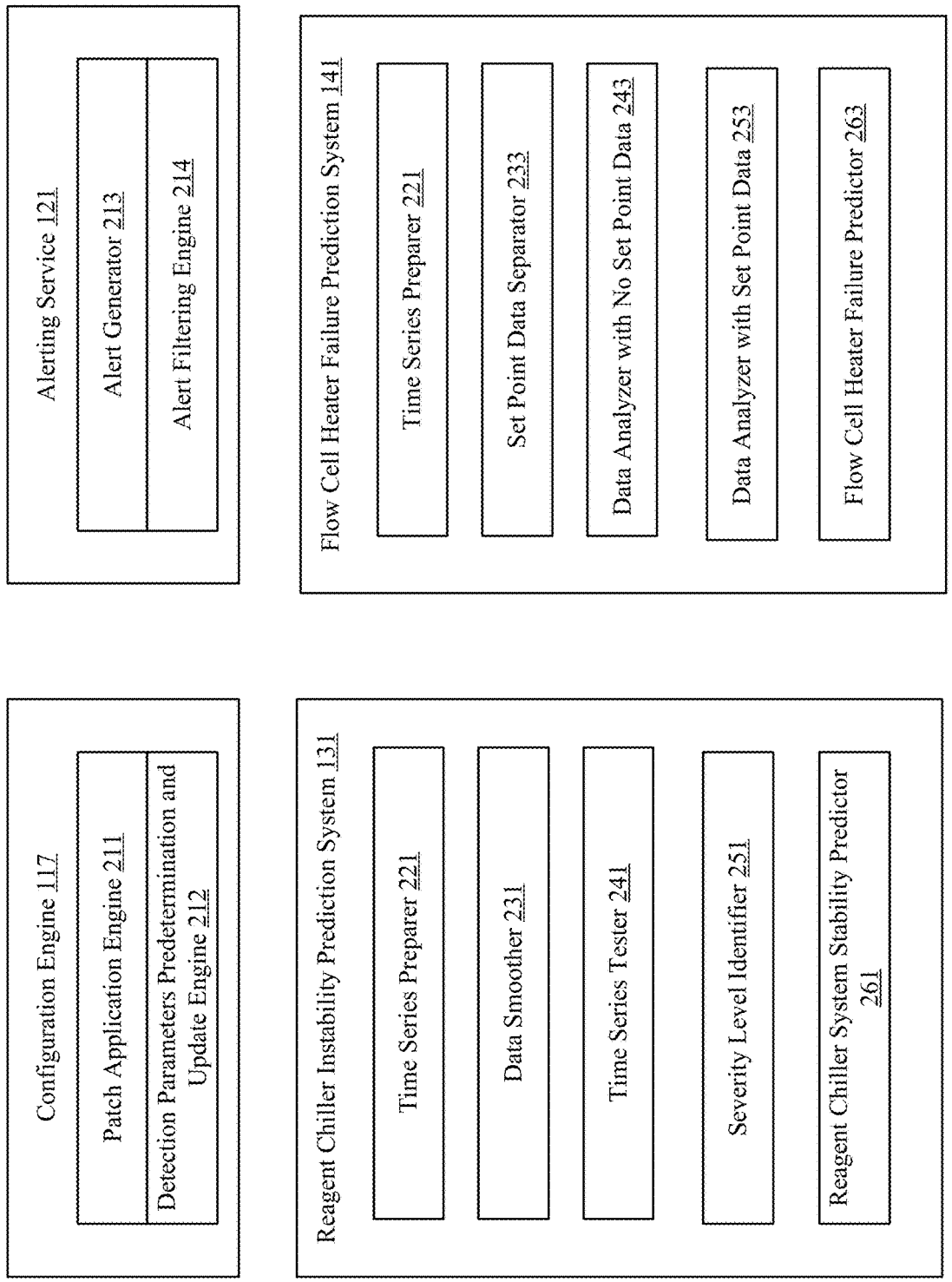
FIG. 2 illustrates subsystem components of reagent chiller instability prediction system and flow cell heater failure prediction system of FIG. 1.

FIG. 2 is a high-level block diagram of components configuration engine 117, alerting service 121, reagent chiller instability prediction system 131, and flow cell heater failure prediction system 141. These systems are computer implemented using a variety of different computer systems as presented below in description of FIG. 8. The illustrated components can be merged or further separated, when implemented.

Configuration Engine

The development team responsible for the so-called proactive alert generation platform investigated what data from sensors used in control loops of sequencing machines could be logged and used to produce leading indicators of approaching malfunctions. Sequencing systems include many sensors and software that can be updated to log a modest number of readings. New signals from closed loops can be identified and analysis developed to yield leading indicator(s) for malfunctions.

For example, the development team determined temperature time series data from the reagent chiller could yield a leading indicator of approaching chiller failure and reagent spoilage. The development team investigated which signals to expose from sensors buried in the sequencing machines. After the signals to be collected were identified, the sequencing machines were retrofitted (and can be configured) to expose the signals. In general, sequencing machines can be supplied patches using the configuration engine 117.

The configuration engine 117 comprises a patch application engine 211 to deploy software programs as patches or updates to existing software program running on the computer controlling the operations of the sequencing machine. The subsystems are computer controlled. Subsystems of the sequencing systems contain sensors producing sensor readings that are used in control loops during operation of the sequencing machines. New systems can be built with equivalent programming.

The newly deployed software patch enables collection and logging of sensor data. For example, the patch application engine 211 can install a software patch to collect temperature sensor readings from the reagent chiller for use in the instability prediction system 131. Similarly, a software patch can be applied to collect flow cell heater sensor readings for the failure prediction system 141. This part of the technology can also be packaged in a sensor exposing module. The configuration engine 117 enables retrofitting of sequencing machines so that previously unlogged data from the sensors in the sequencing machines can be exposed for proactive maintenance.

The configuration engine 117 comprises a detection parameters predetermination and update engine 212. Reliable prediction of an approaching hardware failure involves signal analysis of collected and/or logged sensor readings. The update engine 212 processes at least selected log data exposed from closed loop controls. This data, which was not previously logged, can be collected from multiple geographically-dispersed sequencing machines. Data can be timestamped or sequenced to facilitate correlation or it can be correlated at collection. Data from multiple machines in independent operations increases reliability of the leading indicators of instrument failure.

The detection parameters predetermination and update engine 212 implements the analysis prototyped by the development team, to predetermine—prior to sequencing—detection parameters and filters to apply to the time series data. Examples of analyses that can be used include regression analysis, logit regression, threshold fitting to minimize a cost function and machine learning, if enough failure samples are available. Smoothed rates of change are among the signal features that can be analyzed. An analysis of the leading indicators was performed to determine trends in variations of leading indicators that can predict an approaching malfunction. The detection parameters predetermination and update engine 212 can repeat analysis of the sensor readings in instances of components that failed to predetermine the detection parameters. An example of such analysis is determining the predetermined temperature change rate in instances of the equipment with chiller systems that are approaching consequential malfunctioning.

To improve the quality of maintenance prediction alerts and reduce the number of false alerts, the detection parameters predetermination and update engine 212 could use the service resolution data, following the service calls by the technicians 119, to update the predetermined detection parameters. The service resolution data can include information such as replacement of failed or failing components or false positive indications for the alerts. Existing optimization techniques, such as gradient descent or reapplication of the analyses identified above, can be used to update predetermined detection parameters to reduce the numbers of missed failures and false alerts.

Updates to predetermined detection parameters can be performed periodically after collecting of service calls records over a period of time such as one month, three months or one to 12 months. The update portion of the detection parameters predetermination and update engine can also be packaged in a threshold adjustment module when it processes temperature data from reagent chillers in sequencing systems. The update portion of the detection parameters predetermination and update engine can also be packaged in a temperature margin adjustment module when it processes temperature data from flow cells in sequencing systems.

Alerting Service

Actionable alerts can be generated when failure prediction systems such as the reagent chiller instability prediction system 131 and the flow cell heater failure prediction 141 predict an approaching malfunction. The alerts are passed to the alerting service 121. The alerting service 121 includes an alert generator component 213 which implements, for instance, a service alert subscription and publishing functionality. The alerts are sent to operators 113 and/or technicians 119. A customer relationship management (CRM) system can implement the alerts and track follow-up through resolution.

Filtering can be applied to alerts that recur over multiple cycles of a single run and over multiple sequencing runs, especially for laboratories that have a high utilization rate of sequencing systems 185. The alert filtering engine 214 filters repeat alerts. In one implementation, the system maintains an alerts states database 114 to escalate the service alerts in a planned manner. The CRM system 167 updates the states of the alerts through successive states, such as creation of service ticket, scheduling of service visit and completion of equipment service. The alerting service 121 can escalate service alerts if service actions are not completed within the required service times.

The alerting service 121 can generate more than one type of alert, for example, instrument alerts and run alerts. The instrument alerts are long-lived, typically span across multiple runs and once an alert is generated it remains active until it is resolved. Instrument alerts can require a part replacement or repair. Examples of instrument alerts include reagent chiller instability, flow cell heater failure or laser power failure. Run alerts, on the other hand, can be specific for a sequencing run. In some cases, the operators 113 are able to act on such alerts. For example, the operator can terminate the sequencing run upon receiving an alert identifying a misalignment of the flow cell on the sequencer's flow cell holder. This can save the processing time and sequencing operation costs of a failed run.

Reagent Chiller Instability Prediction System Components

The block diagram presents example components of the two failure prediction systems 131 and 141, which predict instability of reagent chillers and failing flow cell heaters and/or chillers. The time series preparer component 221 is common to both systems 131 and 141. The component 221 prepares a time series from the sequencing hardware metrics. The time series data is collected from sensors in the subsystems of the sequencing systems. The time series preparer 221 can also be packaged in a log collection module. In one implementation the collected data is uploaded to the cloud-based proactive maintenance analyzer 111 and stored in sequencing hardware sensor readings and Q-scores database 151. Examples of temperature sensor time series data for reagent chillers and flow cell heaters are presented in FIGS. 3 and 5. The details of components specific to the reagent chiller instability prediction system 131 and flow cell heater failure prediction system 141 are presented in the following paragraphs.

The reagent chiller instability prediction system 131 further comprises a data smoother 231, a time series tester 241, a severity level identifier 251 and a reagent chiller system stability predictor 261. The reagent chiller temperature sensor data is chronologically sorted in ascending order, if necessary, to prepare the time series. The time series is given as input to a data smoother component 231. As mentioned above, the temperature data from reagent chiller is noisy. The data smoother component 231 filters out transient oscillations in the time series of chiller temperature sensor data. This part of the technology disclosed can also be packaged in a time series smoothing module. In one implementation, the data smoother component 231 applies a derivative filter with a cutoff of 0.125° C. per minute to filter transient oscillations and produce a smoothed time series of chiller temperature sensor data. Alternatively, a filter can be applied that removes the transient oscillations that produce a rate of temperature change of 0.250 degrees Celsius per minute or greater. Or, the smoothing function can remove transient oscillations based on a predetermined rate of temperature change that is greater than or equal to 0.0625 degrees Celsius per minute. An upper limit such as 5.0 degrees Celsius per minute can be built into a filter, but is not necessary.

The reagent chiller prediction system 131 can be implemented as part of the cloud-based proactive maintenance analyzer 111. The logs of temperature sensor data from reagent chiller are analyzed by the configuration engine 117 to predetermine detection parameters as described above. The predetermined detection parameters are used by the time series component 241 to predict chiller system instability. The time series tester component 241 tests the smoothed time series of chiller temperature sensor data in a predefined time window for periods of stable temperature operation. The time series tester component can also be packaged in a temperature instability detection module. The periods of stable temperature operation are defined as the periods of time during which temperature readings in the smoothed time series change by less than a predetermined temperature change rate using the absolute value of the rate of change. In one implementation, the absolute temperature change rate for stable operation is less than 0.05° C. per minute. In another implementation, a higher value can be used e.g. 0.25° C. per minute and alternatively a lower value can be used e.g. 0.01° C. per minute. If the total number of periods of stable temperature operation in a predefined time window are less than a predetermined stability measure, the reagent chiller system stability predictor component 261 determines that the chiller system is unstable and reports if the temperature is rising rapidly (i.e. faster than the above threshold). This number of periods of stable operation can be expressed as a predetermined percentage. The component 261 informs the alerting service 121 that the reagent chiller system is unstable. The reagent chiller system stability predictor component 261 and the alerting service 121 can also be collectively packaged in a temperature instability alert module.

A severity level identifier component 251 compares the mean and median temperatures of a stable chiller system to two thresholds to determine severity level 1 and severity level 2 errors. In one implementation, the configuration engine 117 analyzes the collected temperature sensor readings from reagent chillers in sequencing systems to set the values of the thresholds. For example, such analysis for HISEQX™, HISEQ3000™, and HISEQ4000™ sequencing systems, resulted in setting of a 9° C. threshold for severity level 1 issues and a 7.5° C. threshold for severity level 2 issues. It is understood that different threshold values can be set for severity levels 1 and 2. When severity level identifier 251 determines a chiller system to have severity level 1 or severity level 2 issues, it informs the alerting service 121, which can then generate the alerts.

Flow Cell Heater Failure Prediction System Components

FIG. 2 also shows components of a flow cell heater and/or cooler prediction system 141, including a set point data separator 233, a data analyzer with no set point data component 243, a data analyzer with set point data component 253, and a flow cell heater failure predictor 263. The time series preparer component 221 retrieves temperature sensor data for the flow cell heater from the sequencing hardware sensor readings and Q-scores database 151. In one implementation, the time series preparer component 221 separates the temperature data of side A and side B of the flow cell subsystem. In such an implementation, time series for each side is tested separately.

The temperature sensor data for a flow cell heater is chronologically treated as a time series. The flow cell heater temperature sensor data can be delimited in sequencing process cycles. A processing cycle, also referred to as a base calling cycle, includes multiple chemistry process sub cycles. In one implementation, the duration of a base calling cycle is approximately 15 minutes and the duration of chemistry process sub cycles is approximately 5 minutes.

In one implementation, temperature is reported from the flow cell on the order of every minute during chemistry sub cycles during a base calling cycle. It is understood that in other implementations, samples can be reported at a higher or lower sampling rate, such as in a range of 15 seconds to 3 minutes.

During chemistry process sub cycles, on one sequencer, the temperature ramps up from an initial temperature (e.g., around 20° C.) to a higher temperature (e.g., around 55° C.), stays at this temperature for a short duration, and then ramps up to a further higher temperature (e.g., around 60° C.) for another short duration, and then falls back to initial temperature. These three temperature levels are referred to as set points.

In one implementation, the temperature sensor readings are sampled further apart than the hold duration for a specific temperature point during chemistry sub cycles. In such an implementation, for a small percentage of chemistry sub cycles, no temperature reading is taken at the higher temperatures (55° C. and 60° C.). Therefore, before temperature sensor data for a processing cycle is tested by components 243 or 253, it is checked whether sufficient number of temperature sensor data readings are available. In one implementation, at least 5 readings in a process cycle are required before the data is tested. Alternatively, at least 3 readings may be required or between 3 and 10 readings may be required, depending on chemistry duration and sensor reporting frequency.

The flow cell heater failure prediction system 141 can be implemented as part of the cloud-based proactive maintenance analyzer 111. Sensor data can be analyzed with or without reported set point data. If set point data is available for the flow cell heater temperature sensor then the component 253 analyzes the temperature sensor data using the set point data. There are likely to be more than one temperature set point. The set point data separator module 233 separates the set point data time series from the flow cell heater temperature sensor data time series. Otherwise, if set point data is not available, then the component 243, referred to as data analyzer with no set point data, analyzes the temperature sensor data using an operating heater threshold. This component tests the time series of flow cell heater temperature sensor data to count measured temperature sensor data points in a recent process cycle that were recorded above an operating heater threshold. The threshold is determined based on the likelihood that a sensor measurement was made during specific temperature intervals. In one implementation, the value of the threshold is 31° C., fairly higher than the ambient point, though this threshold can be set as high 54° C., just below the second set point, without significant change in operation. A threshold can be used from a range 10° C. above ambient temperature up to the third set point. Multiple thresholds could be used, in place of one threshold that tracks heating towards the second set point.

This threshold can be established from data analysis, without access to design parameters of the system. When the temperature sensor data does not include set point data, the predetermined threshold analyzer used to predict flow cell heater failure is among detection parameters set by the configuration. The configuration analyzer can use logs of flow cell heater sensor data from sequencers located at multiple locations and operated by multiple independent operators to determine threshold(s) and/or margin(s) above and/or below ambient temperature. In one implementation, the configuration analyzer determines a first predetermined margin above ambient temperature, also referred to as a threshold. The time series from temperature sensors in flow cell heaters are tested to determine if samples in the time series are above the ambient temperature by the first predetermined margin. If the data in temperature time series does not exceed the ambient temperature by the first predetermined margin, the flow cell heater can be failing. More than one consecutive time series corresponding to sequencing cycles can be tested to predict flow cell heater failure.

During the sequencing cycles, the flow cells can also be chilled to below the ambient temperature. To predict the failure of the flow cell cooling to below the ambient temperature, the configuration analyzer can determine a second predetermined margin below ambient temperature, also referred to as a threshold. The configuration analyzer can use logs of flow cell heater sensor data from sequencers located at multiple locations and operated by multiple independent operators to determine this second margin and/or threshold. Time series from temperature sensors in flow cell heaters are tested to determine if samples in the time series are below the ambient temperature by the second predetermined margin. This testing can be early in a base calling cycle, before a predetermined count of sensor measurements during the cycle, if chilling is at the beginning of the cycle. The flow cell heater cooling can be predicted to be failing if the data in one or more than one consecutive sequencing cycles does not drop not below the ambient temperature by the second predetermined margin, below the second threshold.

In a cycle, the number of sensor measurements that satisfy one or more thresholds can be counted. If the count of satisfactory temperature sensor data points in the process cycle being evaluated is less than a predetermined count threshold, test is also applied to obtain the count of flow cell heater temperature data points for a prior (or successive) process cycle immediately preceding (or following) the recent process cycle. If the second count of satisfactory temperature data points for the prior process cycle is less than the predetermined count threshold, in addition to the unsatisfactory first count, the flow cell heater failure predictor 263 determines that the flow cell heater is failing and needs to be serviced. In one implementation, the value of predetermined count threshold is set at 5. The predetermined count threshold can be in a range of 1 to 1000 or higher, depending on chemistry duration and sensor reporting frequency. The component 263 informs the alerting service 121 which sends the alert to a technician. The alerting service 121 can also be packaged in a temperature margin failure alert module. The data analyzer with no set point data component 243 and the flow cell heater failure predictor component 263 can be collectively packaged as a temperature margin detection module.

Data analyzer with set point data 253 compares the flow cell heater temperature data in a recent process cycle with set point data. Like the threshold analysis, if the temperature data is outside a predefined allowable range of the set point data for the recent process cycle, the temperature data for a prior cycle immediately preceding the recent process cycle is tested. The flow cell heater is determined to be failing if flow cell heater temperature data points for two consecutive cycles are outside the predefined allowable range of the set point data. In one implementation, the allowable range is defined as within 2° C. of the set point data. A predetermined count of unsatisfactory temperature data points can be used, as described above for thresholds.

Reagent Chiller Instability Prediction Data and Flow Chart

Figure 3:
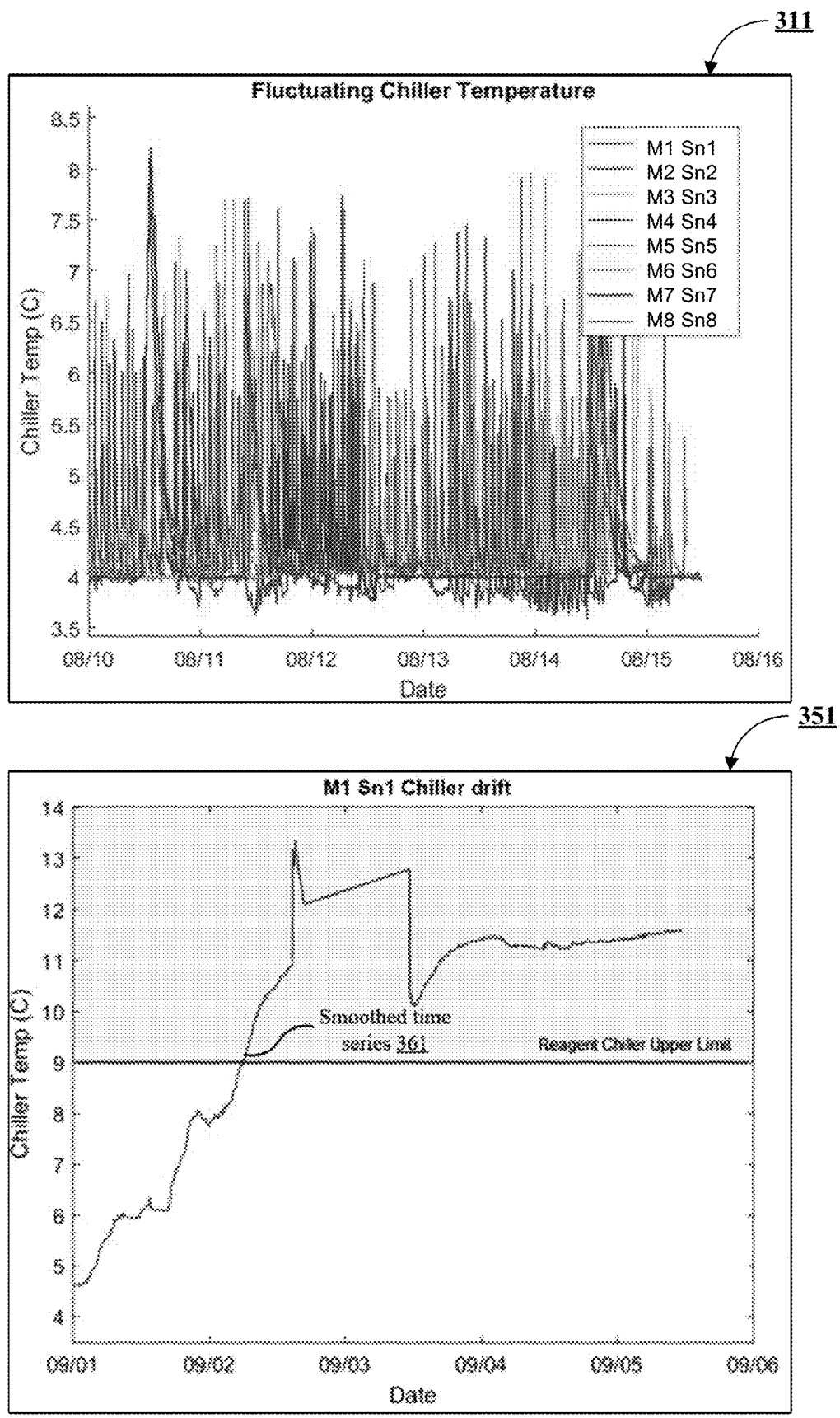
FIG. 3 presents examples of time series of chiller temperature sensor data before and after filtering of noisy data.

FIG. 3 illustrates a time series of chiller temperature sensor data collected from eight sequencing machines M1 to M8. The horizontal axis label indicates that six days of data are reported. The legend on the top right corner of the graph 311 shows serial numbers (Sn1 to Sn8) of eight machines reporting sensor data. As mentioned above, the data is noisy. Several factors contribute to the noise in data such as operation of the mechanical systems used for cooling and condensation in the reagent chillers dripping on the temperature sensor. External factors can also cause temperature variations such as a door of the room, in which the sequencing system is operating, where the door is left open when outside temperature is higher than room temperature. The transient oscillations of temperature, sometimes referred to as high-frequency, are removed from the time series of chiller system temperature sensor data by applying a filter. High-frequency signals have higher derivatives even if the amplitude of the signal is low, and therefore, can cause issues in signal processing. A derivative or other filter with a cut off threshold for frequency can be applied is applied to remove high-frequency or transient oscillations in the chiller temperature sensor data. The derivative filter also removes noise signals with frequencies above the cut-off threshold. The clean temperature profile for sequencing machine M1 with serial number Sn1 is shown in graph 351. In one implementation, noise is filtered out in the smoothed time series 361 using the derivative filter with a cut off of 0.125° C./minute. In another implementation, a higher cut off value such as 0.5° C./minute is used. More generally, a smoothing filter can smooth out oscillations with a predetermined rate of temperature change that is greater than or equal to 0.0625 degrees Celsius per minute and that is less than or equal to 0.50 degrees Celsius per minute.

Periods of steady state of chiller systems are represented by relatively flat, horizontal portions of a smooth line on the graph. The configuration engine 117 analyzes logs of time series of the temperature sensor readings in sequencing systems with chiller system that failed to determine the predetermined temperature change rate to predict unstable chiller systems. The predetermined detection parameters can be updated periodically using service logs of multiple machines. The periods of stable temperature operation are defined as the periods of time during which temperature readings in the smoothed time series change by less than a predetermined temperature change rate using the absolute value of the rate of change. In one implementation, the absolute temperature change rate for stable operation is less than 0.05° C. per minute. In another implementation, a higher value can be used e.g. 0.25° C. per minute and alternatively a lower value can be used e.g. 0.01° C. per minute, or in a range from 0.01° C. to 0.25° C. per minute. The steadiness criteria should not overlap with the smoothing filter parameters, or the filter will steady all data analysis.

The technology disclosed can analyze the number of periods of stable operation, in a time window, of the chiller system to predict an unstable chiller system. In one implementation, the chiller system is considered in a stable operation if total time of steady state periods is at least 14 hours in a 24 hour time window. In other implementations, time series of chiller temperature sensor data for shorter time windows can be analyzed to identify periods of steady state, such as one to 20 hours. In such implementations, the chiller system stability is predicted by testing multiple shorter time series. The configuration engine 117 analyzes logs of time series of the temperature sensor readings in sequencing systems with chiller system that failed to determine the predetermined number of steady state periods in a time window to predict unstable chiller systems.

The graph 361 shows the temperature is increasing and crosses above the 9° C. upper limit during first half of the second day ($2^{nd}$ September). If temperature increase is due to external factors, then an alarm that the chiller system is unstable should not be raised. Suppose, the increase in temperature is due to an external factor such as warm air coming in the room due to a door left opened. The temperature falls back as the external factor is removed, such as when the door is closed. If this happens in a relatively short time, reagents are unlikely to be spoiled.

The technology disclosed differentiates between influence of external factors on chiller system instability, thus reducing false alerts. In one implementation, the technology disclosed includes a predetermined detection parameter defining for how long the chiller system is allowed to operate above the upper limit temperature (9° C.) before an alarm is raised. In such an implementation, the technology disclosed observes the reversal of trends in the temperature graph 361. If analysis of data in the graph indicates the temperature is decreasing towards the upper limit (9° C.) then the technology disclosed determines an expected time at which the chiller system temperature will fall back in the normal operating temperature range. The total time a chiller system is expected to remain above the upper limit (9° C.) is compared with the time allowed to operate above reagent chiller upper limit. The alarm is not raised if the total expected time above the upper limit is less than the time allowed above the upper limit. The detection parameters set by the configuration engine 117 are used by the reagent chiller instability prediction system 131 to test time series data collected from temperature sensors in chiller systems. The process steps can also be illustrated by a flowchart 400.

Figure 4:
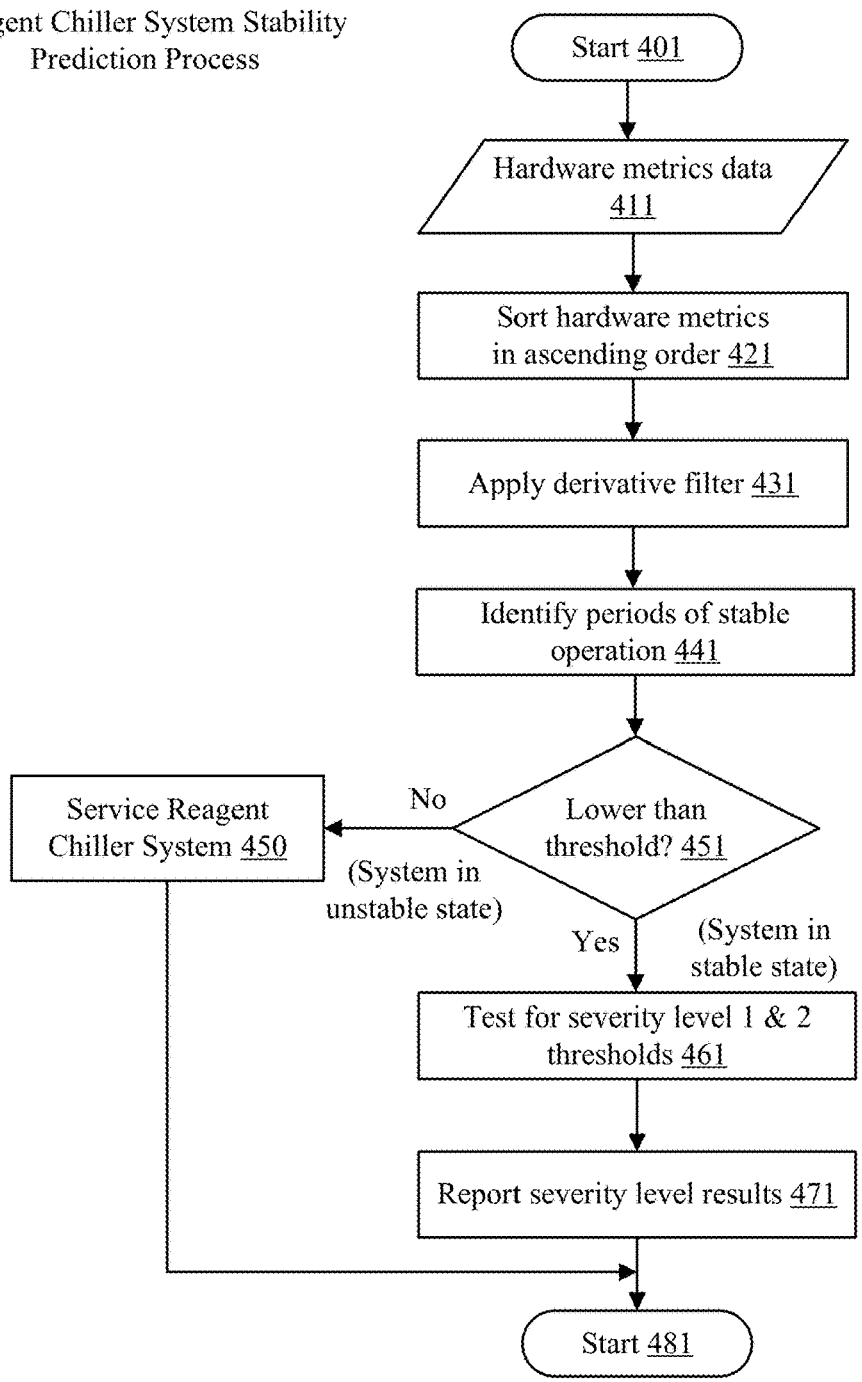
FIG. 4 is a flowchart illustrating process steps to predict reagent chiller system instability by reagent chiller failure prediction system of FIG. 1.

FIG. 4 is an example flowchart illustrating one implementation of the reagent chiller system stability prediction process 400. The process starts at step 401, the temperature sensor data from sequencing hardware sensor readings and Q-scores database 151 is given as input at step 411. As discussed above, the data includes a time series of chiller temperature sensor data. At step 421, the time series data is sorted chronologically. A derivative filter is applied at step 431 to remove noisy data. Periods of stable operation of the chiller system in a predefined time window are identified at step 341. At step 451, the count of periods of stable operation is compared with a threshold. If the count is less than the threshold, an alert is sent to the alerting service 121 that chiller system needs service (step 450). If the count of periods of stable operation is greater than the threshold, the chiller temperature sensor data is tested for severity level 1 and severity level 2 errors at step 361 using respective thresholds. Results of severity level testing are reported at step 371. The process ends at step 381.

FLOW CELL HEATER FAILURE PREDICTION DATA AND FLOW CHART

Figure 5:
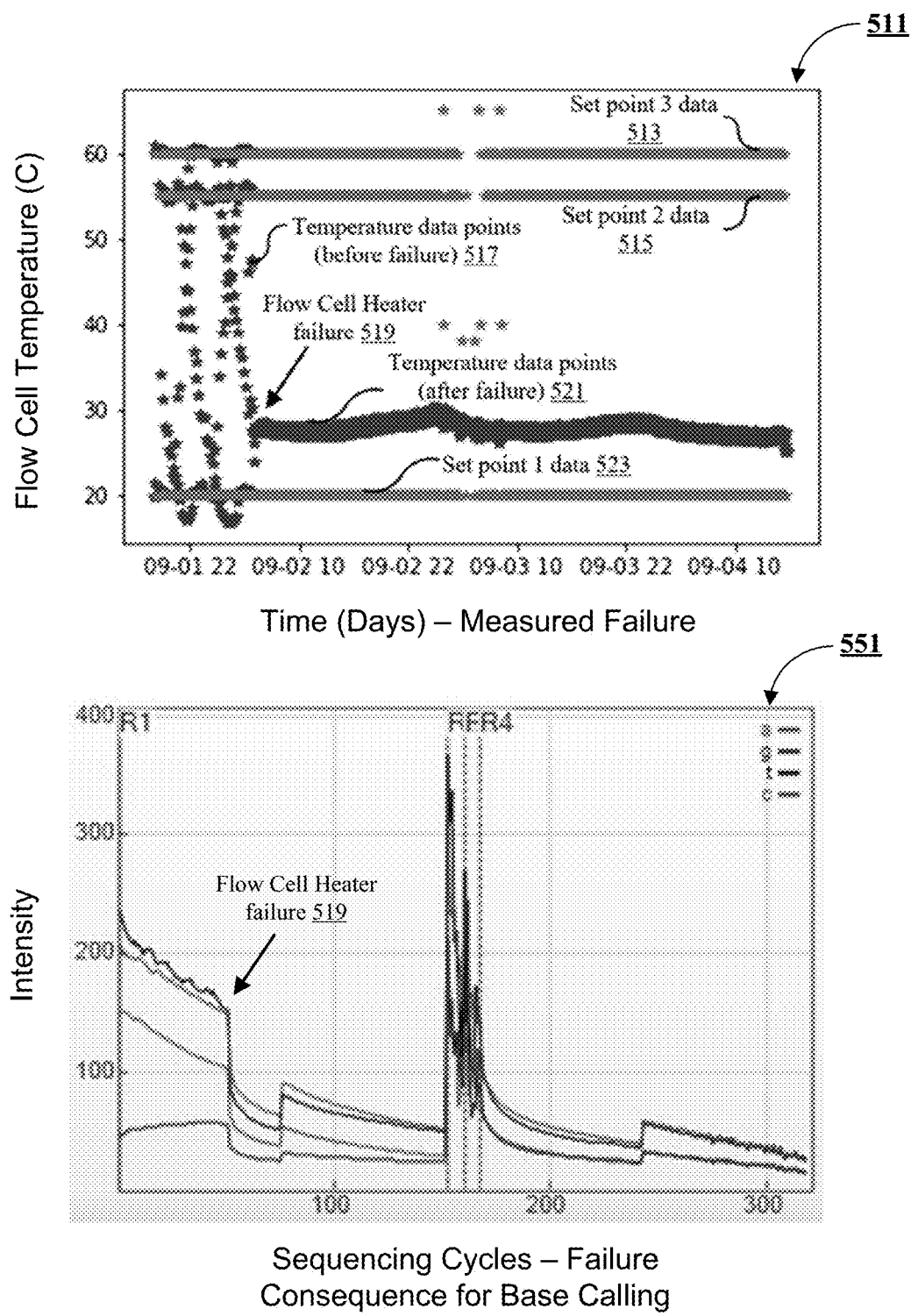
FIG. 5 shows an example time series of flow cell heater temperature sensor data before and after failure of the flow cell heater.

FIG. 5 includes graph 511 of an example time series of flow cell heater temperature sensor data for a sequencing run completed in three days, with an accompanying set point time series. At the start of a processing cycle, the temperature of the flow cell is around 20° C. As the chemistry process in the cycle proceeds, the temperature of the flow cell ramps up to 55° C. for a brief moment of time and up to 60° C. for another brief moment. At the end of the cycle, the temperature of the flow cell falls back to 20° C. and stays there until the chemistry process in the next cycle. This pattern of temperature ramp up and cool down of the flow cell is repeated in each process cycle. There are three time series of set point data as shown in the graph 511. The time series of set point 1 data 523 corresponds to 20° C. temperature level, the time series of set point 2 data 615 corresponds to 55° C. and the time series of set point 3 data 513 corresponds to 60° C.

The graph 511 illustrates that the flow cell heater is working normally in the beginning of the sequencing run. As the processing cycles proceed, the flow cell temperature follows the normal operation of ramp up and cool down according to the set point data (517). The current set point data is intended to be a time sequence that goes up and down over time through the process. In the figure, the three set points look like continuous lines, because three days of data are graphed on a short horizontal axis, but the current set point actually goes up and down. However, the flow cell heater fails around the middle of the first day of operation as indicated by a label 519 on the graph. After flow cell heater failure, the temperature of the flow cell remains at the ambient level (521) and does not follow the ramp up and cool down to three set points. The failure of flow cell heater results in failure of subsequent base calling of A, G, T, and C bases as shown in the graph 551. The intensities of the four channels corresponding to the four bases decreases sharply at the same moment as the flow cell heater fails. Note that temperature sensor data time series 517 and 521 as shown in graph 511 represent the data from both flow cells on side A and side B. The failure of both flow cells at the same time is likely due to an upstream error (e.g., power failure, control board failure, etc.). For flow cell heater time series data that does not include set point data, the predetermined detection parameters determined by the configuration engine 117 are used to determine the flow cell heater failure. Two examples of such predetermined detection parameters include, the first predetermined margin and the second predetermined margin as explained above in system description of flow cell heater failure prediction system (FIG. 2). The process to test the flow cell heater temperature time series data using the set point data or the predetermined detection parameters is presented in the flow chart below.

Figure 6:
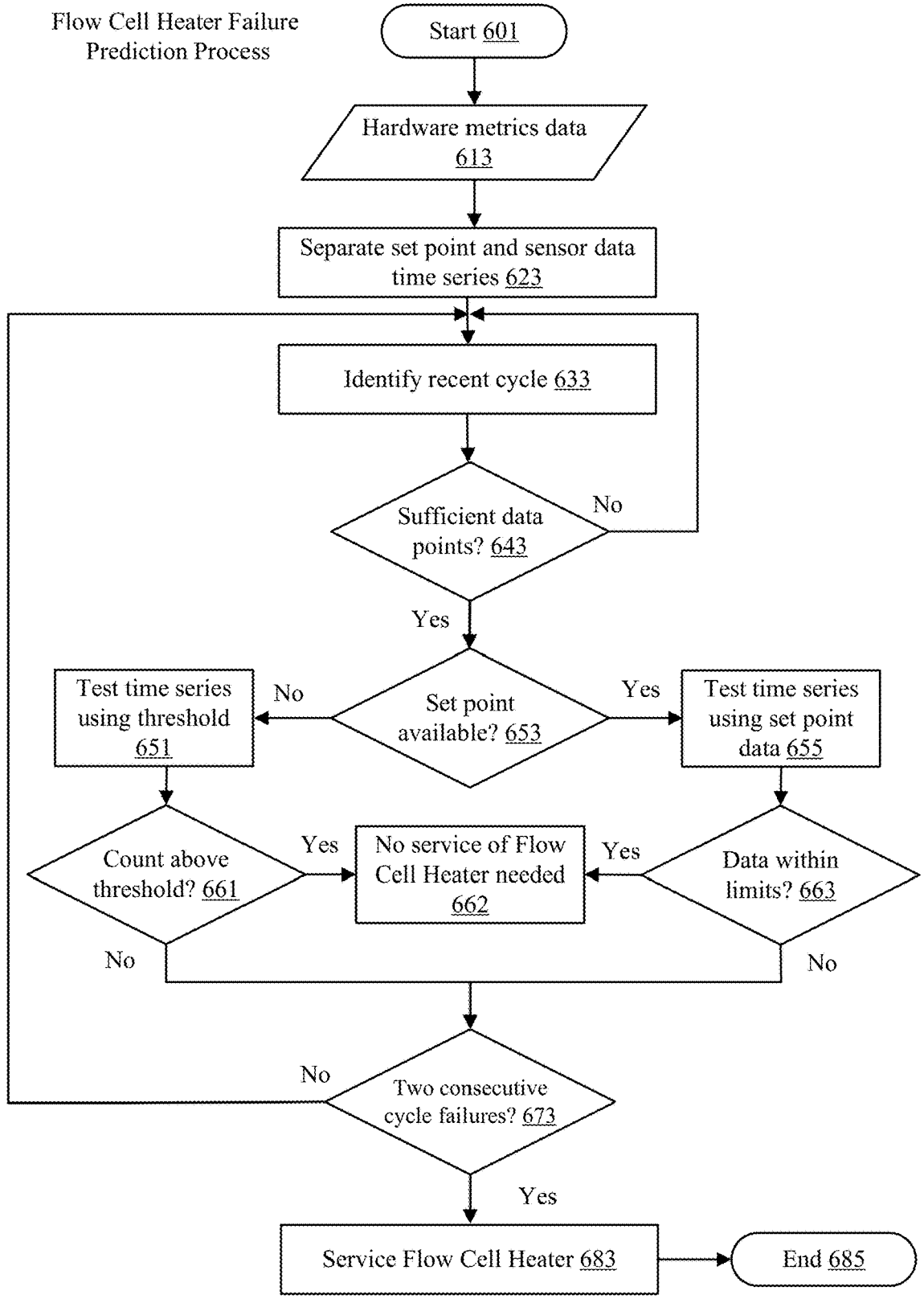
FIG. 6 is a flowchart of process steps for detecting flow cell heater failure by the flow cell heater failure prediction system of FIG. 1 with and without set point data.

FIG. 6 is an example flowchart illustrating one implementation of a flow cell heater and/or cooler failure prediction process. The process starts at step 601. The hardware metrics data is given as input at step 613. As mentioned above the hardware metrics include flow cell heater temperature sensor data time series and set point data time series. The set point data time series is separated from the temperature sensor data time series at step 623. At step 633, flow cell heater temperature sensor data for a recent process cycle is identified. If there are sufficient data points in the recent process cycle (step 643), the flow cell heater failure prediction process continues at step 653, otherwise steps 633 and 643 are repeated for a prior process cycle immediately preceding the recent process cycle. In one implementation, at least five flow cell heater temperature sensor data points for a process cycle are required to meet the condition of sufficient data points at step 543.

At step 653, it is determined whether set point data is available. If set point data is available, then time series of flow cell heater temperature sensor data for the recent cycle is tested at step 655. The temperature data is tested to check whether it is within a predefined allowable range of the set point data at step 663. If the data values are within the predefined allowable range, the control moves to step 662 indicating that the flow cell heater is operating normally and does not require any service. Otherwise, the control moves to step 673. If set point data are not available, then a time series of flow cell heater temperature sensor data is tested using a threshold using the first predetermined margin above the ambient temperature as defined above in FIG. 2. If count of the data points is above threshold, flow cell heater does not require any service (step 662). Otherwise, the above process of testing the temperature data points for a process cycle are repeated for a prior process cycle immediately preceding (or following) the recent process cycle. If the testing fails in two consecutive process cycles, it is determined that the flow cell heater requires service (step 683). The process completes at step 685.

Figure 7:
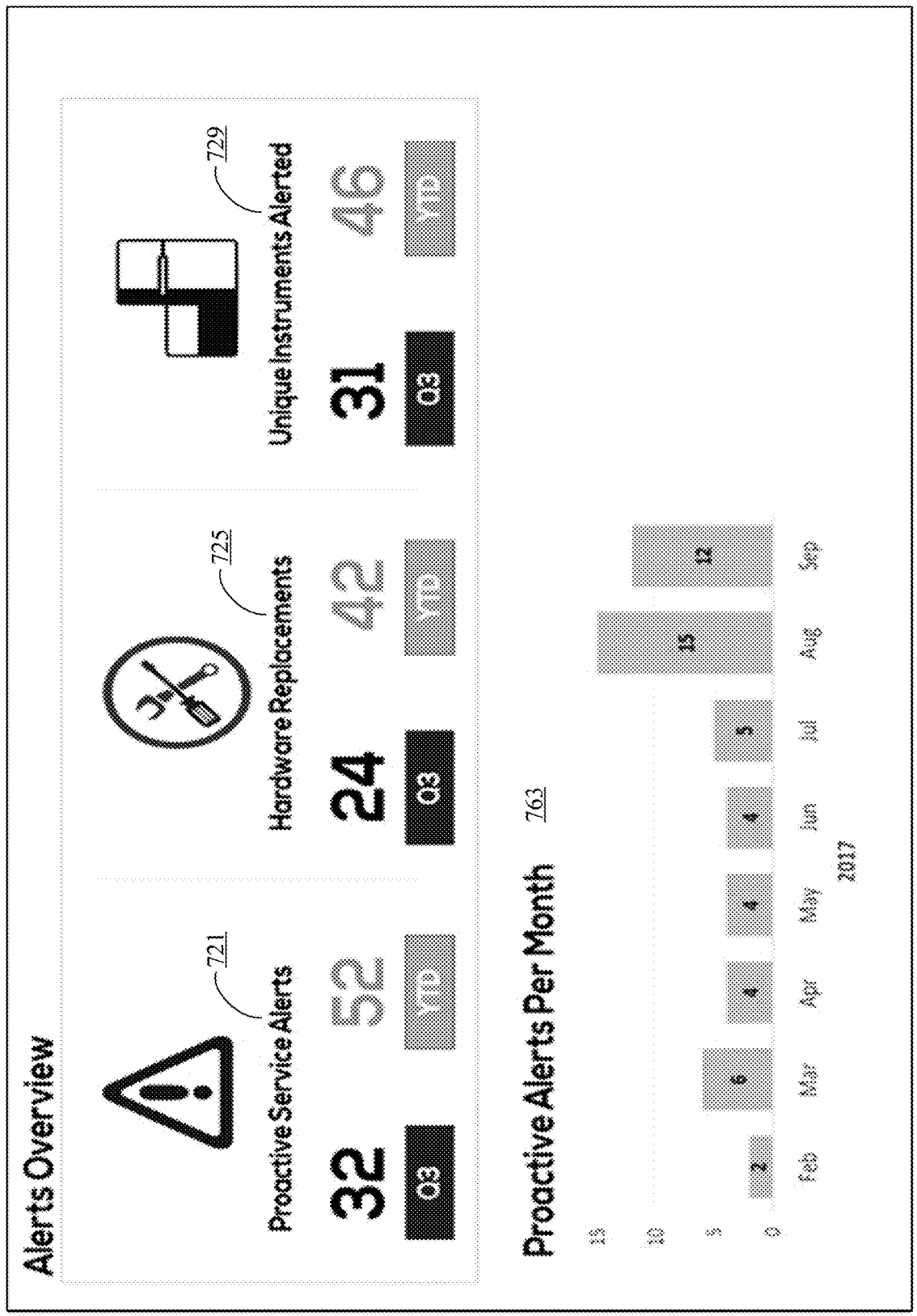
FIG. 7 presents an example user interface to present results of proactive monitoring of sequencing systems to predict hardware failures.

FIG. 7 is an example user interface that can be used to present service alerts for sequencing systems (721). The results can also indicate the number of alerts that resulted in hardware replacement (725) and the number of unique sequencing instruments for which the alerts were generated (729). A month-wise distribution of alerts can also be presented graphically (763). These alerts are expected to reduce unplanned downtime of the sequencing system.

COMPUTER SYSTEM

Figure 8:
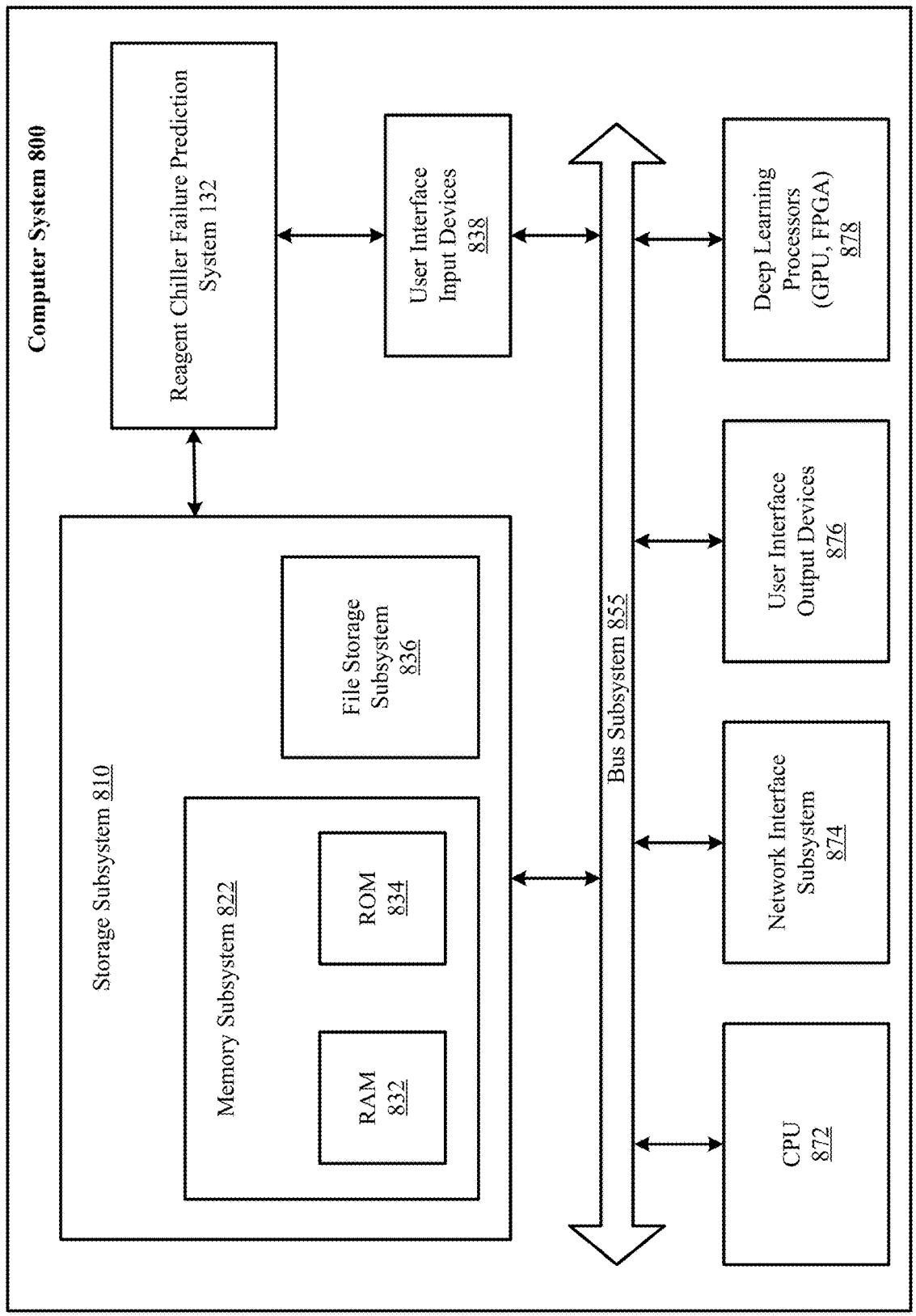
FIG. 8 is a simplified block diagram of a computer system that can be used to implement the reagent chiller instability prediction system and flow cell heater failure prediction system of FIG. 1.

FIG. 8 is a simplified block diagram of a computer system 800 that can be used to implement the reagent chiller failure prediction system 131 of FIG. 1 to detect chiller system instability. A similar computer system 900 can be used to implement the flow cell heater failure prediction system 141 of FIG. 1 to detect flow cell heater failure over multiple cycles. Computer system 800 includes at least one central processing unit (CPU) 872 that communicates with a number of peripheral devices via bus subsystem 855. These peripheral devices can include a storage subsystem 810 including, for example, memory devices and a file storage subsystem 836, user interface input devices 838, user interface output devices 876, and a network interface subsystem 874. The input and output devices allow user interaction with computer system 800. Network interface subsystem 874 provides an interface to outside networks, including an interface to corresponding interface devices in other computer systems.

In one implementation, the reagent chiller failure prediction system 131 of FIG. 1 is communicably linked to the storage subsystem 810 and the user interface input devices 838. In another implementation, the flow cell heater failure prediction system 141 of FIG. 1 is communicably linked to the storage subsystem 810 and the user interface input devices 838.

User interface input devices 838 can include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" is intended to include all possible types of devices and ways to input information into computer system 800.

User interface output devices 876 can include a display subsystem, a printer, a fax machine, or non-visual displays such as audio output devices. The display subsystem can include an LED display, a cathode ray tube (CRT), a flat-panel device such as a liquid crystal display (LCD), a projection device, or some other mechanism for creating a visible image. The display subsystem can also provide a non-visual display such as audio output devices. In general, use of the term "output device" is intended to include all possible types of devices and ways to output information from computer system 800 to the user or to another machine or computer system.

Storage subsystem 810 stores programming and data constructs that provide the functionality of some or all of the modules and methods described herein. These software modules are generally executed by deep learning processors 878.

Deep learning processors 878 can be graphics processing units (GPUs) or field-programmable gate arrays (FPGAs). Deep learning processors 878 can be hosted by a deep learning cloud platform such as Google Cloud Platform™, Xilinx™, and Cirrascale™. Examples of deep learning processors 878 include Google's Tensor Processing Unit (TPU)™, rackmount solutions like GX4 Rackmount Series™, GX8 Rackmount Series™, NVIDIA DGX-1™ Microsoft' Stratix V FPGA™, Graphcore's Intelligent Processor Unit (IPU)™, Qualcomm's Zeroth Platform™ with Snapdragon Processors™, NVIDIA's Volta™, NVIDIA's DRIVE PX™ NVIDIA's JETSON TX1/TX2 MODULE™, Intel's Nirvana™, Movidius VPU™, Fujitsu DPI™, ARM's DynamicIQ™, IBM TrueNorth™, and others.

Memory subsystem 822 used in the storage subsystem 810 can include a number of memories including a main random access memory (RAM) 832 for storage of instructions and data during program execution and a read only memory (ROM) 834 in which fixed instructions are stored. A file storage subsystem 836 can provide persistent storage for program and data files, and can include a hard disk drive, a floppy disk drive along with associated removable media, a CD-ROM drive, an optical drive, or removable media cartridges. The modules implementing the functionality of certain implementations can be stored by file storage subsystem 836 in the storage subsystem 910, or in other machines accessible by the processor.

Bus subsystem 855 provides a mechanism for letting the various components and subsystems of computer system 800 communicate with each other as intended. Although bus subsystem 855 is shown schematically as a single bus, alternative implementations of the bus subsystem can use multiple busses.

Computer system 800 itself can be of varying types including a personal computer, a portable computer, a workstation, a computer terminal, a network computer, a television, a mainframe, a server farm, a widely-distributed set of loosely networked computers, or any other data processing system or user device. Due to the ever-changing nature of computers and networks, the description of computer system 800 depicted in FIG. 8 is intended only as a specific example for purposes of illustrating a particular implementation of the technology disclosed. Many other configurations of computer system 800 are possible having more or less components than the computer system depicted in FIG. 8.

The preceding description is presented to enable the making and use of the technology disclosed. Various modifications to the disclosed implementations will be apparent, and the general principles defined herein may be applied to other implementations and applications without departing from the spirit and scope of the technology disclosed. Thus, the technology disclosed is not intended to be limited to the implementations shown, but is to be accorded the widest scope consistent with the principles and features disclosed herein. The scope of the technology disclosed is defined by the appended claims.

PARTICULAR IMPLEMENTATIONS

Reagent Chiller Instability Prediction System

The technology disclosed relates to detection of chiller system instability that reduces false alerts.

The technology disclosed can be practiced as a system, method, or article of manufacture. One or more features of an implementation can be combined with the base implementation. Implementations that are not mutually exclusive are taught to be combinable. One or more features of an implementation can be combined with other implementations. This disclosure periodically reminds the user of these options. Omission from some implementations of recitations that repeat these options should not be taken as limiting the combinations taught in the preceding sections—these recitations are hereby incorporated forward by reference into each of the following implementations.

A first system implementation of the technology disclosed includes one or more processors and memory coupled to the processors. The memory is loaded with computer instructions to detect chiller system instability configured to produce fewer false alerts than a simple threshold alarm. The computer instructions, when executed on the processors, apply a smoothing function to a time series of chiller temperature sensor data to reduce transient oscillations. The transient oscillations of temperature are sometimes referred to as high-frequency oscillations. The application of function produces a smoothed time series of chiller temperature sensor data. The system tests the smoothed time series of chiller temperature sensor data in a predefined time window for periods of stable temperature operation. The temperature readings in the smoothed time series change by less than a predetermined temperature change rate. The system determines the chiller system to be unstable when less than 50 percent of the time window is stable and reports a need for service when periods of stable temperature operation total less than a predetermined stability measure.

This system implementation and other systems disclosed optionally include one or more of the following features. System can also include features described in connection with methods disclosed. In the interest of conciseness, alternative combinations of system features are not individually enumerated. Features applicable to systems, methods, and articles of manufacture are not repeated for each statutory class set of base features. The reader will understand how features identified in this section can readily be combined with base features in other statutory classes.

The system determines the predetermined temperature change rate based on equipment located at multiple locations and operated by multiple independent operators. The system includes logic that causes configuration of the equipment to log and report temperature sensor readings and store the collected logs of the temperature sensor readings. The system includes analyzing time series of the temperature sensor readings in instances of the equipment with chiller systems that failed and determines predetermined temperature change rate. The predetermined temperature change rate is stored for use in the determining of the chiller system to be unstable.

The system includes updating the predetermined temperature change rate based on equipment located at multiple locations and operated by multiple independent operators. The system includes logic that causes configuration of the equipment to log and report temperature sensor readings. The system collects and stores logs of the temperature sensor readings and logs of service following the notifications of the unstableness. The system includes analyzing time series of the temperature sensor readings in instances of the equipment with chiller systems that generated the notifications and service following the notifications. The system determines an update to the predetermined temperature change rate based on the analysis of the time series of the temperature sensor readings and service record data following the notifications. The system stores the updated predetermined temperature change rate for use in the determining of the chiller system to be unstable.

The system includes a cloud based proactive maintenance analyzer to access logs of the temperature sensor readings from a particular chiller system. The cloud based proactive maintenance analyzer performs the application of the smoothing function, the determination that the smoothed time series of chiller temperature sensor data in a predefined time window fails a stable temperature operation criteria and the generation of the notifications.

The system filters out repeat notifications and submits the filtered notifications to a customer relations management system for tracking. The system filters out repeat notifications and submits the filtered notifications to an operator of sequencer that includes the chiller system.

There can be at least 50 multiple locations at which sequencing systems are located. The sequencing systems can be operated by at least 20 independent operators.

This system can require a higher degree of stability, applying a predetermined stability measure of 75 or 90 percent of the time window. The time window can be between four and 48 hours. One choice of time window can be about 24 hours. Another choice is six to 36 hours.

This system can use a derivative filter to apply the smoothing function to the time series data. The smoothing function can be tuned to remove transient oscillations that produce a rate of temperature change of 0.125 or 0.25 degrees Celsius per minute or greater. Or it can be tuned to remove transient oscillations that produce a rate of temperature change of greater than or equal to 0.625 degrees Celsius per minute and that is less than or equal to 0.50 degrees Celsius per minute.

The system can use a criterion of temperature changes of less than 0.010, 0.05 or 0.25 degrees Celsius per minute as the predetermined stability measure, or in a range between any of these criteria.

The system can automatically accompany a report of a system unstableness determination with the smoothed chiller system temperature sensor data for review by a user, in either a graph or table.

The system includes comparing average and median temperatures and for periods of stable operation and reporting a severity level 1 error above a first threshold. The system also includes reporting a severity level 2 error if the average and median temperatures for periods of stable operation are above a second threshold.

The system includes applying the derivative filter that removes transient oscillations with a rate of absolute change of temperature of at least 0.125 degrees Celsius per minute. The system includes testing the smoothed time series of chiller temperature sensor data in a predefined time window for periods of stable temperature operation during which temperature readings in the smoothed time series change by less than a predetermined absolute temperature change rate of 0.05 degrees Celsius per minute.

Other implementations may include a non-transitory computer readable storage medium storing instructions executable by a processor to perform functions of the system described above. Yet another implementation may include a method performing the functions of the system described above.

A second system implementation of the technology disclosed includes one or more processors and memory coupled to the processors. The memory is loaded with computer instructions to detect and alert a technician that sequencer has an unstable chiller system. The alerting system includes a time series smoothing module that receives temperature sensor data from a sensor exposed in the chiller system of the sequencer and produces a smoothed temperature time series. A temperature instability detection module receives the smoothed temperature time series. The temperature instability detection module reports changes between smoothed successive datum in the smoothed temperature time series that exceed a predetermined temperature change as unstable and determines a degree of instability. The system includes a temperature instability alert module that receives the reports of the degree of instability and generates an alert to a technician when the degree of instability exceeds a predetermined threshold.

This system implementation and other systems disclosed optionally include one or more of the following features. System can also include features described in connection with methods disclosed. In the interest of conciseness, alternative combinations of system features are not individually enumerated. Features applicable to systems, methods, and articles of manufacture are not repeated for each statutory class set of base features. The reader will understand how features identified in this section can readily be combined with base features in other statutory classes.

The system comprises a sensor exposing module on the sequencer that exposes a temperature sensor in the chiller system and reports temperature sensor data from the exposed temperature sensor. The system includes a log collection module that receives the temperature sensor data from multiple devices including the sequencer. The collection module makes the temperatures sensor data from the chiller system of the sequencer available to the time series smoothing module.

The system can update various predetermined detection parameters for use by the alerting system. Three examples of updates to predetermined detection parameters are presented below.

The system includes a threshold updating component that modifies the predetermined threshold. The threshold updating component further includes a log collection module and a threshold adjustment module. The log collection module receives the temperature sensor data from multiple devices including the sequencer. The log collection module makes the temperature sensor data from the chiller system of the sequencer available to the threshold adjustment module. The threshold adjustment module receives new temperature sensor data, modifies the predetermined threshold based on the new temperature sensor data, and stores the modified predetermined threshold for use by the temperature instability alert module.

The system includes a threshold updating component that modifies the predetermined temperature change. The threshold updating component further includes a log collection module and a threshold adjustment module. The log collection module receives the temperature sensor data from multiple devices including the sequencer. The log collection module makes the temperature sensor data from the chiller system of the sequencer available to the threshold adjustment module. The threshold adjustment module receives new temperature sensor data, modifies the predetermined temperature change based on the new temperature sensor data, and stores the modified predetermined temperature change for use by the temperature instability detection module.

The system includes a threshold updating component that modifies the parameters for the smoothing module. The threshold updating component further includes a log collection module and a threshold adjustment module. The log collection module receives the temperature sensor data from multiple devices including the sequencer. The log collection module makes the temperature sensor data from the chiller system of the sequencer available to the threshold adjustment module. The threshold adjustment module receives new temperature sensor data, modifies the parameters for the smoothing module based on the new temperature sensor data, and stores the modified parameters for the smoothing for use by the time series smoothing module.

The threshold updating component and the system further comprise a customer relations module and a threshold adjustment module. The customer relations module tracks alerts, failures and resolutions for multiple devices including the sequencer. The threshold adjustment module further receives failure and resolution data from the customer relations module. It distinguishes between missed failures and false alerts when modifying parameters used by any of the time series smoothing module, the temperature instability detection module, or the temperature instability alert module.

Other implementations may include a non-transitory computer readable storage medium storing instructions executable by a processor to perform functions of the system described above. Yet another implementation may include a method performing the functions of the system described above.

A first method implementation of the technology disclosed includes detecting chiller system instability that reduces false alerts. The method includes applying a smoothing function to a time series of chiller temperature sensor data to reduce transient oscillations. The application of filter produces a smoothed time series of chiller temperature sensor data. The method includes testing the smoothed time series of chiller temperature sensor data in a predefined time window for periods of stable temperature operation. The temperature readings in the smoothed time series change by less than a predetermined temperature change rate. Finally, the method determines the chiller system to be unstable and reports a need for service when periods of stable temperature operation total less than a predetermined stability measure.

This method implementation and other methods disclosed optionally include one or more of the following features. Methods can also include features described in connection with systems disclosed. The reader will understand how features identified in this section can readily be combined with base features in other statutory classes.

The method includes determining the predetermined temperature change rate based on equipment located at multiple locations and operated by multiple independent operators. The method includes causing configuration of the equipment to log and report temperature sensor readings and store the collected logs of the temperature sensor readings. The method includes analyzing time series of the temperature sensor readings in instances of the equipment with chiller systems that failed and determining the predetermined temperature change rate. The predetermined temperature change rate is stored for use in the determining of the chiller system to be unstable.

The method includes updating the predetermined temperature change rate based on equipment located at multiple locations and operated by multiple independent operators. The method includes causing configuration of the equipment to log and report temperature sensor readings. The method includes collecting and storing temperature sensor readings and logs of service following the notifications of the unstableness. The method includes analyzing time series of the temperature sensor readings in instances of the equipment with chiller systems that generated the notifications and service following the notifications. The method includes determining an update to the predetermined temperature change rate based on the analysis of the time series of the temperature sensor readings and service record data following the notifications. The updated predetermined temperature change rate is stored for use in the determining of the chiller system to be unstable.

The method includes accessing logs of the temperature sensor readings from a particular chiller system. The method includes applying the smoothing function to determine that the smoothed time series of chiller temperature sensor data in a predefined time window fails a stable temperature operation criteria and the generation of the notifications.

The method includes filtering out repeat notifications and submitting the filtered notifications to a customer relations management system for tracking. The method includes filtering out repeat notifications and submitting the filtered notifications to an operator of sequencer that includes the chiller system.

There can be at least 50 multiple locations at which sequencing systems are located. The sequencing systems can be operated by at least 20 independent operators.

The use of this method can require a higher degree of stability, applying a predetermined stability measure of 75 or 90 percent of the time window. The time window can be between four and 48 hours. One choice of time window can be about 24 hours. Another choice is six to 36 hours.

This method can include using a derivative filter to apply the smoothing function to the time series data. The smoothing function can be tuned to remove transient oscillations that produce a rate of temperature change of 0.125 or 0.25 degrees Celsius per minute or greater. Or it can be tuned to remove transient oscillations that produce a rate of temperature change of greater than or equal to 0.625 degrees Celsius per minute and that is less than or equal to 0.50 degrees Celsius per minute.

The method can include using a criterion of temperature changes of less than 0.010, 0.05 or 0.25 degrees Celsius per minute as the predetermined stability measure, or in a range between any of these criteria.

The method can include automatically accompanying a report of a system unstableness determination with the smoothed chiller system temperature sensor data for review by a user, in either a graph or table.

The method includes comparing average and median temperatures and for periods of stable operation and reporting a severity level 1 error above a first threshold. The method also includes reporting a severity level 2 error if the average and median temperatures for periods of stable operation are above a second threshold.

The method includes applying the derivative filter that removes transient oscillations with a rate of absolute change of temperature of at least 0.125 degrees Celsius per minute. The system includes testing the smoothed time series of chiller temperature sensor data in a predefined time window for periods of stable temperature operation during which temperature readings in the smoothed time series change by less than a predetermined absolute temperature change rate of 0.05 degrees Celsius per minute.

Each of the features discussed in this particular implementation section for the system implementation apply equally to this method implementation. As indicated above, all the system features are not repeated here and should be considered repeated by reference.

Other implementations may include a set of one or more non-transitory computer readable storage media collectively storing computer program instructions executable by one or more processors to detect chiller system instability. The computer program instructions when executed on or more processors implement the method including, detecting chiller system instability that reduces false alerts. The method includes applying a smoothing function to a time series of chiller temperature sensor data to reduce transient oscillations. The application of filter produces a smoothed time series of chiller temperature sensor data. The method includes testing the smoothed time series of chiller temperature sensor data in a predefined time window for periods of stable temperature operation. The temperature readings in the smoothed time series change by less than a predetermined temperature change rate. Finally, the method determines the chiller system to be unstable and reports a need for service when periods of stable temperature operation total less than a predetermined stability measure. Yet another implementation may include a system including memory and one or more processors operable to execute instructions, stored in the memory, to perform the first method described above.

Computer readable media (CRM) implementations of the technology disclosed include one or more a non-transitory computer readable storage media impressed with computer program instructions, when executed on one or more processors, implement the method described above.

This CRM implementation includes one or more of the following features. CRM implementation can also include features described in connection with system and method disclosed above. The method includes determining the predetermined temperature change rate based on equipment located at multiple locations and operated by multiple independent operators. The method includes causing configuration of the equipment to log and report temperature sensor readings and store the collected logs of the temperature sensor readings. The method includes analyzing time series of the temperature sensor readings in instances of the equipment with chiller systems that failed and determining the predetermined temperature change rate. The predetermined temperature change rate is stored for use in the determining of the chiller system to be unstable.

The CRM-implemented method includes updating the predetermined temperature change rate based on equipment located at multiple locations and operated by multiple independent operators. The method includes causing configuration of the equipment to log and report temperature sensor readings. The method includes collecting and storing temperature sensor readings and logs of service following the notifications of the unstableness. The method includes analyzing time series of the temperature sensor readings in instances of the equipment with chiller systems that generated the notifications and service following the notifications. The method includes determining an update to the predetermined temperature change rate based on the analysis of the time series of the temperature sensor readings and service record data following the notifications. The updated predetermined temperature change rate is stored for use in the determining of the chiller system to be unstable.

The CRM-implemented method includes accessing logs of the temperature sensor readings from a particular chiller system. The method includes applying the smoothing function to determine that the smoothed time series of chiller temperature sensor data in a predefined time window fails a stable temperature operation criteria and the generation of the notifications.

The CRM-implemented method includes filtering out repeat notifications and submitting the filtered notifications to a customer relations management system for tracking. The method includes filtering out repeat notifications and submitting the filtered notifications to an operator of sequencer that includes the chiller system.

There can be at least 50 multiple locations at which sequencing systems are located. The sequencing systems can be operated by at least 20 independent operators.

The use of this method can require a higher degree of stability, applying a predetermined stability measure of 75 or 90 percent of the time window. The time window can be between four and 48 hours. One choice of time window can be about 24 hours. Another choice is six to 36 hours.

This CRM-implemented method can include using a derivative filter to apply the smoothing function to the time series data. The smoothing function can be tuned to remove transient oscillations that produce a rate of temperature change of 0.125 or 0.25 degrees Celsius per minute or greater. Or it can be tuned to remove transient oscillations that produce a rate of temperature change of greater than or equal to 0.625 degrees Celsius per minute and that is less than or equal to 0.50 degrees Celsius per minute.

The CRM-implemented method can include using a criterion of temperature changes of less than 0.010, 0.05 or 0.25 degrees Celsius per minute as the predetermined stability measure, or in a range between any of these criteria.

The CRM-implemented method can include automatically accompanying a report of a system unstableness determination with the smoothed chiller system temperature sensor data for review by a user, in either a graph or table.

The CRM-implemented method includes comparing average and median temperatures and for periods of stable operation and reporting a severity level 1 error above a first threshold. The method also includes reporting a severity level 2 error if the average and median temperatures for periods of stable operation are above a second threshold.

The CRM-implemented method includes applying the derivative filter that removes transient oscillations with a rate of absolute change of temperature of at least 0.125 degrees Celsius per minute. The system includes testing the smoothed time series of chiller temperature sensor data in a predefined time window for periods of stable temperature operation during which temperature readings in the smoothed time series change by less than a predetermined absolute temperature change rate of 0.05 degrees Celsius per minute.

A second method implementation of the technology disclosed includes detecting that a sequencer has an unstable chiller system. The method includes receiving temperature sensor data obtained from a sensor exposed in the chiller system of the sequencer. The method includes applying a smoothing function to the temperature sensor data to produce a smoothed temperature time series. The method includes determining changes between smoothed successive datum in the smoothed temperature time series that exceed a predetermined temperature change. The method includes determining a degree of instability based upon the determined changes. The method includes generating an alert indicating that the sequence has an unstable chiller system when the degree of instability exceeds a predetermined threshold.

This method implementation and other methods disclosed optionally include one or more of the following features. Methods can also include features described in connection with systems disclosed. The reader will understand how features identified in this section can readily be combined with base features in other statutory classes.

The temperature sensor data is determined based on sensors located at multiple locations and operated by multiple independent operators. The method includes causing configuration of equipment to log and report temperature sensor readings. The method includes collecting logs of the temperature sensor readings. The method includes analyzing time series of the temperature sensor readings in instances of the equipment with chiller systems that failed and determining the predetermined temperature change. The method includes storing the predetermined temperature change for use in the determining of the degree of instability.

The method further comprises, receiving the temperature sensor data from multiple devices including the sequencer. The method includes receiving new temperature sensor data from the multiple devices. The method includes modifying the predetermined threshold based on the new temperature sensor data and storing the modified predetermined threshold for generating the alert.

The method further comprises, receiving the temperature sensor data from multiple devices including the sequencer. The method includes receiving new temperature sensor data from the multiple devices. The method includes modifying the predetermined temperature change based on the new temperature sensor data. The method includes storing the modified predetermined temperature change for determining changes that exceed a predetermined temperature change.

The method includes threshold updating comprising, receiving the temperature sensor data from multiple devices including the sequencer. The method includes receiving new temperature sensor data from the multiple devices. The method includes modifying parameters for the smoothing function based on the new temperature sensor data and storing the modified parameters for the smoothing function.

The method includes tracking alerts, failures and resolutions for multiple devices including the sequencer. The method includes receiving failure and resolution data from a customer relations module. The method includes distinguishing between missed failures and false alerts when modifying parameters of the smoothing function, determining a degree of instability, or the generating an alert.

The smoothing function is applied by a derivative filter. Applying the smoothing function removes transient oscillations that produce a rate of temperature change of 0.125 degrees Celsius per minute or greater.

The method includes comparing average and median temperatures for periods of stable operation and reporting a first degree of instability when the average and median temperatures vary by more than a first threshold.

The method includes comparing average and median temperatures for periods of stable operation and reporting a second degree of instability when the average and median temperatures vary by more than a second threshold.

A system implementation of the technology comprises one or more processors coupled to memory, the memory loaded with computer instructions that when executed by the one or more processors cause the system to carry out a method according to any one of methods described above. Each of the features discussed above in this particular implementation section for the second method implementation apply equally to this system implementation.

A CRM implementation of the technology comprises a non-transitory computer readable storage media impressed with computer program instructions. The instructions, when executed on one or more processors, implement a method according to any of the methods presented above.

Each of the features discussed in this particular implementation section for the system implementation apply equally to the CRM implementation. As indicated above, all the system features are not repeated here and should be considered repeated by reference.

Flow Cell Heater Failure Prediction System

The technology disclosed relates to detection of flow cell heater failure over multiple cycles in a system with no set point.

A first system implementation of the technology disclosed includes one or more processors and memory coupled to the processor. The memory is loaded with computer instructions detecting flow cell heater failure over multiple cycles in a system with no set point. The computer instructions, when executed on the processors, testing a time series of flow cell heater temperature sensor data across base calling cycles to determine whether the most recent or next to most recent base calling cycle has enough flow cell heater temperature sensor data points to be evaluated. The count of cell heater temperature sensor data points that is enough to be evaluated corresponds, in some implementations, to a time in the base calling cycles at which the flow cell heater temperature is supposed to exceed the ambient operating temperature by more than a first predetermined margin. The instructions further carry out determining whether latest flow cell heater temperature sensor data in the evaluated cycle exceed an ambient operating temperature by a first predetermined margin. Upon failure of the evaluated cycle flow cell heater temperature sensor data to exceed the operating temperature by the first predetermined margin, determining whether flow cell heater temperature sensor data in a successive cycle, immediately following the evaluated cycle, exceed the ambient operating temperature by the first predetermined margin. Then, upon failure of the evaluated cycle flow cell heater temperature sensor data to exceed the operating temperature by the first predetermined margin in both the evaluated cycle and the successive cycle, determining the flow cell heater to be failing and reporting a need for service.

This system implementation and other systems disclosed optionally include one or more of the following features. System can also include features described in connection with methods disclosed. In the interest of conciseness, alternative combinations of system features are not individually enumerated. Features applicable to systems, methods, and articles of manufacture are not repeated for each statutory class set of base features. The reader will understand how features identified in this section can readily be combined with base features in other statutory classes.

The system determines the first predetermined margin based on equipment located at multiple locations and operated by multiple independent operators. The system includes logic that causes configuration of the equipment to log and report temperature sensor readings and store the collected logs of the temperature sensor readings. The system includes logic to analyze time series of the temperature sensor readings in instances of the equipment with flow cells heaters that failed and determines the first predetermined margin. The first predetermined temperature margin is stored for use in the determining of the flow cell heater to be failing.

The system updates the first predetermined margin based on equipment located at multiple locations and operated by multiple independent operators. The system includes logic that causes configuration of the equipment to log and report temperature sensor readings and logs of service following the reporting the need for service. The system stores the collected logs. The system includes analyzing time series of the temperature sensor readings in instances of the equipment with flow cells heaters that were healthy and that failed and the logs of service following the reporting of need for service. The system determines an update to the first predetermined margin based on the analysis.

The system includes a cloud based proactive maintenance analyzer to access logs of the temperature sensor readings from a particular flow cell heater. The cloud based proactive maintenance analyzer performs the application of the testing, the determining and the reporting the need for service from the cloud based proactive maintenance analyzer.

The system filters out repeat notifications and submits the filtered notifications to a customer relations management system for tracking. The system filters out repeat notifications and submits the filtered notifications to an operator of sequencer that includes the flow cell heater system.

The system determines whether a count of cell heater temperature sensor data points corresponding to a time in the base calling cycles at which the flow cell heater temperature is supposed to exceed the ambient operating temperature is enough to be evaluated by more than the first predetermined margin.

On the low side of temperatures, when the flow cell is supposed to be cooled below ambient, instructions can further carry out determining whether one or more cell heater temperature sensor data points in the evaluated, taken prior to the count, is less wherein the ambient operating temperature minus a second predetermined margin. Upon failure of the evaluated cycle flow cell heater temperature sensor data to be less than the operating temperature by the second predetermined margin, determining whether flow cell heater temperature sensor data taken prior to the count in a successive cycle, immediately following the evaluated cycle, is less than the ambient operating temperature by the second predetermined margin. Then, upon failure of the evaluated cycle flow cell heater temperature sensor data to be less than the operating temperature by the second predetermined margin in both the evaluated cycle and the successive cycle, determining flow cell cooling to be failing and reporting a need for service.

The system determines the second predetermined margin based on equipment located at multiple locations and operated by multiple independent operators. The system includes logic that causes configuration of the equipment to log and report temperature sensor readings and store the collected logs of the temperature sensor readings. The system includes analyzing time series of the temperature sensor readings in instances of the equipment with flow cells heaters that failed and determines second predetermined margin. The second predetermined temperature margin is stored for use in the determining of the flow cell heater to be failing.

The system updates the second predetermined margin based on equipment located at multiple locations and operated by multiple independent operators. The system includes logic that causes configuration of the equipment to log and report temperature sensor readings and logs of service following the reporting the need for service. The system stores the collected logs. The system includes analyzing time series of the temperature sensor readings in instances of the equipment with flow cells heaters that were healthy and that failed and the logs of service following the reporting of need for service. The system determines an update to the second predetermined margin based on the analysis.

Other implementations may include a non-transitory computer readable storage medium storing instructions executable by a processor to perform functions of the system described above. Yet another implementation may include a method performing the functions of the system described above.

A second system implementation includes an alerting system for detecting and alerting a technician that a sequencer has a failing flow cell temperature control system. A temperature detection module analyzes a time series of flow cell temperature sensor data across base calling cycles. The temperature margin detection module determines whether the most recent or next to most recent base calling cycle has enough flow cell temperature sensor data points to be evaluated. It also determines whether the temperature sensor data in the evaluated cycle exceeded an ambient operating temperature by a first predetermined margin. Upon failure of the evaluated cycle flow cell temperature sensor data to exceed the ambient operating temperature by the first predetermined margin, the flow cell temperature sensor data in a successive cycle, immediately before or following the evaluated cycle, is determined. If the flow cell temperature sensor data in the successive cycle fails to exceed the ambient operating temperature by the first predetermined margin, the temperature margin detection module sets a first failure condition. The system also includes a temperature margin failure alert module that receives the determination of the first failure condition and that generates a flow cell heater alert to a technician.

This system implementation and other systems disclosed optionally include one or more of the following features. System can also include features described in connection with methods disclosed. In the interest of conciseness, alternative combinations of system features are not individually enumerated. Features applicable to systems, methods, and articles of manufacture are not repeated for each statutory class set of base features. The reader will understand how features identified in this section can readily be combined with base features in other statutory classes.

The temperature margin detection module is further configured to determine flow cell chiller failure by analyzing the time series of flow cell heater temperature sensor data across base calling cycles. The system determines whether the most recent or next to most recent base calling cycle has flow cell temperature sensor data points to be evaluated during a flow cell chilling subcycle. The system determines whether the temperature sensor data in the evaluated cycle was chilled below an ambient operating temperature by a second predetermined margin. Upon failure of the evaluated cycle flow cell temperature sensor data to fall below the ambient operating temperature by the second predetermined margin, the system determines the flow cell heater temperature sensor data in a successive cycle, immediately before or following the evaluated cycle. If the successive cycle temperature sensors data failed to fall below the ambient operating temperature by the second predetermined margin, the system sets a second failure condition. The temperature margin failure alert module receives the determination of the second failure condition and generates a flow cell chiller alert to a technician.

The system includes a sensor exposing module on the sequencer that exposes a temperature sensor in the flow cell temperature control system. The sensor exposing module also reports temperature sensor data from the exposed temperature sensor. A log collection module receives the temperature sensor data from multiple devices, including the sequencer. The log collection module makes the temperature sensor data from the flow cell temperature control system of the sequencer available to the temperature margin detection module.

The system includes updating the temperature margin. A log collection module receives the temperature sensor data from multiple devices including the sequencer. The log collection module makes the temperature sensor data from the flow cell temperature control system of the sequencer available to a temperature margin adjustment module. The temperature margin adjustment module receives new temperature sensor data from the multiple devices. It modifies the first predetermined margin based on the new temperature sensor data, and stores the modified first predetermined threshold for use by the temperature margin failure alert module.

The system includes updating the temperature margin. A log collection module receives the temperature sensor data from multiple devices including the sequencer. The log collection module makes the temperature sensor data from the flow cell temperature control system of the sequencer available to a temperature margin adjustment module. The temperature margin adjustment module receives new temperature sensor data from the multiple devices. It modifies the second predetermined margin based on the new temperature sensor data, and stores the modified second predetermined threshold for use by the temperature margin failure alert module.

The system utilizes CRM data in temperature margin updates. A customer relations module that tracks alerts, failures and resolutions for multiple devices including the sequencer. The temperature margin adjustment module receives failure and resolution data from the customer relations module. It distinguishes between missed failures and false alerts when modifying parameters implemented by the temperature margin adjustment module.

Other implementations may include a non-transitory computer readable storage medium storing instructions executable by a processor to perform functions of the system described above. Yet another implementation may include a method performing the functions of the system described above.

A first method implementation of the technology disclosed includes detecting flow cell heater failure over multiple cycles in a system with no set point. The method includes testing a time series of flow cell heater temperature sensor data that is delimited in process cycles to determine how many points in a recent process cycle were recorded above a threshold. The threshold is determined based on the likelihood of the measurement being made during specific temperature intervals. When a first count of the points recorded in the recent process cycle is less than a predetermined count threshold, the method repeats the testing for a prior process cycle immediately preceding the recent process cycle and determines how many points in the prior process cycle were recorded above the threshold. The threshold is determined based on the likelihood of the measurement being made during specific temperature intervals. When a second count of the points recorded in the prior process cycle is less than the predetermined count threshold in addition to the first count of the points recorded in the prior process cycle is less than the predetermined count threshold, the method determines the flow cell heater to be failing and reporting a need for service.

This method implementation and other methods disclosed optionally include one or more of the following features. Methods can also include features described in connection with systems disclosed. The reader will understand how features identified in this section can readily be combined with base features in other statutory classes.

The method includes determining the first predetermined margin based on equipment located at multiple locations and operated by multiple independent operators. The method includes causing configuration of the equipment to log and report temperature sensor readings and store the collected logs of the temperature sensor readings. The method includes analyzing time series of the temperature sensor readings in instances of the equipment with flow cells heaters that failed and determining the first predetermined margin. The first predetermined temperature margin is stored for use in the determining of the flow cell heater to be failing.

The method includes updating the first predetermined margin based on equipment located at multiple locations and operated by multiple independent operators. The method includes causing configuration of the equipment to log and report temperature sensor readings and logs of service following the reporting the need for service. The method includes storing the collected logs. The method includes analyzing time series of the temperature sensor readings in instances of the equipment with flow cells heaters that were healthy and that failed and the logs of service following the reporting of need for service. The method includes determining an update to the first predetermined margin based on the analysis.

The method includes accessing logs of the temperature sensor readings from a particular flow cell heater. The method includes performing the application of the testing, the determining and the reporting the need for service from the cloud based proactive maintenance analyzer.

The method includes filtering out repeat notifications and submitting the filtered notifications to a customer relations management system for tracking. The method includes filtering out repeat notifications and submitting the filtered notifications to an operator of sequencer that includes the flow cell heater system.

The method includes determining whether a count of cell heater temperature sensor data points corresponding to a time in the base calling cycles at which the flow cell heater temperature is supposed to exceed the ambient operating temperature is enough to be evaluated by more than the first predetermined margin.

On the low side of temperatures, when the flow cell is supposed to be cooled below ambient, instructions can further carry out determining whether one or more cell heater temperature sensor data points in the evaluated, taken prior to the count, is less wherein the ambient operating temperature minus a second predetermined margin. Upon failure of the evaluated cycle flow cell heater temperature sensor data to be less than the operating temperature by the second predetermined margin, determining whether flow cell heater temperature sensor data taken prior to the count in a successive cycle, immediately following the evaluated cycle, is less than the ambient operating temperature by the second predetermined margin. Then, upon failure of the evaluated cycle flow cell heater temperature sensor data to be less than the operating temperature by the second predetermined margin in both the evaluated cycle and the successive cycle, determining flow cell cooling to be failing and reporting a need for service.

The method includes determining the second predetermined margin based on equipment located at multiple locations and operated by multiple independent operators. The method includes logic that causes configuration of the equipment to log and report temperature sensor readings and store the collected logs of the temperature sensor readings. The method includes analyzing time series of the temperature sensor readings in instances of the equipment with flow cells heaters that failed and determining second predetermined margin. The second predetermined temperature margin is stored for use in the determining of the flow cell heater to be failing.

The method includes updating the second predetermined margin based on equipment located at multiple locations and operated by multiple independent operators. The method includes causing configuration of the equipment to log and report temperature sensor readings and logs of service following the reporting the need for service. The method includes storing the collected logs. The method includes analyzing time series of the temperature sensor readings in instances of the equipment with flow cells heaters that were healthy and that failed and the logs of service following the reporting of need for service. The method includes determining an update to the second predetermined margin based on the analysis.

Other implementations may include a set of one or more non-transitory computer readable storage media collectively storing computer program instructions executable by one or more processors. The computer program instructions when executed on or more processors implement the method including, detecting that a flow cell heater is failing over multiple cycles in a base calling system. The method includes testing a time series of flow cell heater temperature sensor data that is delimited in process cycles to determine how many points in a recent process cycle were recorded above a threshold. The threshold is determined based on the likelihood of the measurement being made during specific temperature intervals. When a first count of the points recorded in the recent process cycle is less than a predetermined count threshold, the method repeats the testing for a prior process cycle immediately preceding the recent process cycle and determines how many points in the prior process cycle were recorded above the threshold. The threshold is determined based on the likelihood of the measurement being made during specific temperature intervals. When a second count of the points recorded in the prior process cycle is less than the predetermined count threshold in addition to the first count of the points recorded in the prior process cycle is less than the predetermined count threshold, the method determines the flow cell heater to be failing and reporting a need for service.

This method implementation and other methods disclosed optionally include one or more of the following features. Methods can also include features described in connection with systems disclosed. The reader will understand how features identified in this section can readily be combined with base features in other statutory classes.

The CRM-implemented method includes determining the first predetermined margin based on equipment located at multiple locations and operated by multiple independent operators. The method includes causing configuration of the equipment to log and report temperature sensor readings and store the collected logs of the temperature sensor readings. The method includes analyzing time series of the temperature sensor readings in instances of the equipment with flow cells heaters that failed and determining the first predetermined margin. The first predetermined temperature margin is stored for use in the determining of the flow cell heater to be failing.

The CRM-implemented method includes updating the first predetermined margin based on equipment located at multiple locations and operated by multiple independent operators. The method includes causing configuration of the equipment to log and report temperature sensor readings and logs of service following the reporting the need for service. The method includes storing the collected logs. The method includes analyzing time series of the temperature sensor readings in instances of the equipment with flow cells heaters that were healthy and that failed and the logs of service following the reporting of need for service. The method includes determining an update to the first predetermined margin based on the analysis.

The CRM-implemented method includes accessing logs of the temperature sensor readings from a particular flow cell heater. The method includes performing the application of the testing, the determining and the reporting the need for service from the cloud based proactive maintenance analyzer.

The CRM-implemented method includes filtering out repeat notifications and submitting the filtered notifications to a customer relations management system for tracking. The method includes filtering out repeat notifications and submitting the filtered notifications to an operator of sequencer that includes the flow cell heater system.

The CRM-implemented method includes determining whether a count of cell heater temperature sensor data points corresponding to a time in the base calling cycles at which the flow cell heater temperature is supposed to exceed the ambient operating temperature is enough to be evaluated by more than the first predetermined margin.

On the low side of temperatures, when the flow cell is supposed to be cooled below ambient, instructions can further carry out determining whether one or more cell heater temperature sensor data points in the evaluated, taken prior to the count, is less wherein the ambient operating temperature minus a second predetermined margin. Upon failure of the evaluated cycle flow cell heater temperature sensor data to be less than the operating temperature by the second predetermined margin, determining whether flow cell heater temperature sensor data taken prior to the count in a successive cycle, immediately following the evaluated cycle, is less than the ambient operating temperature by the second predetermined margin. Then, upon failure of the evaluated cycle flow cell heater temperature sensor data to be less than the operating temperature by the second predetermined margin in both the evaluated cycle and the successive cycle, determining flow cell cooling to be failing and reporting a need for service.

The CRM-implemented method includes determining the second predetermined margin based on equipment located at multiple locations and operated by multiple independent operators. The method includes logic that causes configuration of the equipment to log and report temperature sensor readings and store the collected logs of the temperature sensor readings. The method includes analyzing time series of the temperature sensor readings in instances of the equipment with flow cells heaters that failed and determining second predetermined margin. The second predetermined temperature margin is stored for use in the determining of the flow cell heater to be failing.

The CRM-implemented method includes updating the second predetermined margin based on equipment located at multiple locations and operated by multiple independent operators. The method includes causing configuration of the equipment to log and report temperature sensor readings and logs of service following the reporting the need for service. The method includes storing the collected logs. The method includes analyzing time series of the temperature sensor readings in instances of the equipment with flow cells heaters that were healthy and that failed and the logs of service following the reporting of need for service. The method includes determining an update to the second predetermined margin based on the analysis.

A second method implementation of the technology disclosed includes detecting that a sequencer has a failing flow cell temperature control system. The method includes analyzing a time series of flow cell temperature sensor data across base calling cycles. This further includes determining whether a first base calling cycle has enough flow cell temperature sensor data points to satisfy a count threshold. The method includes determining whether the temperature sensor data in the first cycle exceeded an ambient operating temperature by a first predetermined margin. Upon failure of the flow cell temperature sensor data in the first cycle to exceed the ambient operating temperature by the first predetermined margin, the method includes determining that the flow cell temperature sensor data in a second, contiguous cycle, immediately before or following the first cycle has enough flow cell temperature sensor data points to satisfy the count threshold. The method further includes determining that the flow cell temperature sensor data in the second contiguous cycle fails to exceed the ambient operating temperature by the first predetermined margin. The method then responsively setting a first failure condition. The method includes generating a flow cell heater alert responsive to the first failure condition.

This method implementation and other methods disclosed optionally include one or more of the following features. Methods can also include features described in connection with systems disclosed. The reader will understand how features identified in this section can readily be combined with base features in other statutory classes.

The method includes determining flow cell chiller failure by analyzing the time series of flow cell heater temperature sensor data across base calling cycles. This further includes determining that the first base calling cycle has flow cell temperature sensor data points to be evaluated during a flow cell chilling subcycle. The method includes determining whether the temperature sensor data in the first cycle was chilled below an ambient operating temperature by a second predetermined margin. Upon failure of the flow cell temperature sensor data to chill below the ambient operating temperature by the second predetermined margin in the first cycle, the method includes determining that the flow cell heater temperature sensor data in the second, contiguous cycle, immediately before or following the first cycle, failed to chill below the ambient operating temperature by the second predetermined margin. Following this, the method includes setting a second failure condition. The method includes generating a flow cell chiller alert responsive to the second failure condition.

The method includes exposing a temperature sensor in the flow cell temperature control system and reporting temperature sensor data from the exposed temperature sensor. The method includes receiving the temperature sensor data from multiple devices, including the sequencer. The method includes applying the analyzing a time series of flow cell temperature sensor data across a plurality of base calling cycles to the temperature sensor data from the multiple devices.

The method including temperature margin updating, comprising, receiving the temperature sensor data from multiple devices including the sequencer. The method further comprising receiving new temperature sensor data from the multiple devices. The method further comprising modifying the first predetermined margin based on the new temperature sensor data, and storing the modified first predetermined margin.

The method including temperature margin updating, comprising, receiving the temperature sensor data from multiple devices including the sequencer. The method further comprising, receiving new temperature sensor data from the multiple devices. The method including modifying the second predetermined margin based on the new temperature sensor data, and storing the modified second predetermined margin.

The method utilizing CRM data in temperature margin updating, comprising, tracking alerts, failures and resolutions for multiple devices including the sequencer. The method further comprising, receiving failure and resolution data from the customer relations module and distinguishing between missed failures and false alerts when modifying parameters implemented by the temperature margin adjustment module.

A system implementation of the technology comprises one or more processors coupled to memory, the memory loaded with computer instructions that when executed by the one or more processors cause the system to carry out a method according to any one of methods described above. Each of the features discussed above in this particular implementation section for the second method implementation apply equally to this system implementation.

A CRM implementation of the technology comprises a non-transitory computer readable storage media impressed with computer program instructions. The instructions, when executed on one or more processors, implement a method according to any of the methods presented above.

Each of the features discussed in this particular implementation section for the system implementation apply equally to the CRM implementation. As indicated above, all the system features are not repeated here and should be considered repeated by reference.

I claim as follows:

1. A method of detecting chiller system instability comprising:
    applying a smoothing function to a time series of chiller temperature sensor data and reducing transient oscillations to produce a smoothed time series of chiller temperature sensor data;
    determining that the smoothed time series of chiller temperature sensor data in a predefined time window fails a stable temperature operation criteria in time intervals during which temperature readings in the smoothed time series change by more than a predetermined temperature change rate from interval to interval; and
    generating a notification of unstableness when the smoothed time series of chiller temperature sensor data fails the stable temperature operation criteria in more than a predetermined percentage of the time intervals over the predefined time window.

2. The method of claim 1, further comprising:
    determining the predetermined temperature change rate based on equipment located at multiple locations and operated by multiple independent operators, including:
        causing configuration of the equipment to log and report temperature sensor readings;
        collecting logs of the temperature sensor readings;
        analyzing time series of the temperature sensor readings in instances of the equipment with chiller systems that failed and determining the predetermined temperature change rate; and
        storing the predetermined temperature change rate for use in the determining of the chiller system to be unstable.

3. The method of claim 1, further comprising:
    updating the predetermined temperature change rate based on equipment located at multiple locations and operated by multiple independent operators, including:
        causing configuration of the equipment to log and report temperature sensor readings;
        collecting logs of the temperature sensor readings and logs of service following the notifications of the unstableness;
        analyzing time series of the temperature sensor readings in instances of the equipment with chiller systems that generated the notifications and service following the notifications;
        determining an update to the predetermined temperature change rate based on the analyzing; and
        storing the updated predetermined temperature change rate for use in the determining of the chiller system to be unstable.

4. The method of claim 1, further comprising:
    accessing logs of the temperature sensor readings from a particular chiller system in a cloud based proactive maintenance analyzer; and
    performing the applying, the determining and the generating the notification from the cloud based proactive maintenance analyzer.

5. The method of claim 4, further comprising filtering notifications for repeat notification and submitting the filtered notifications to a customer relations management system for tracking.

6. The method of claim 4, further comprising filtering notifications for repeat notification and submitting the filtered notifications to an operator of sequencer that includes the chiller system.

7. The method of claim 2, further including determining the predetermined temperature change rate based on equipment located at the multiple locations and operated by the multiple independent operators, wherein the multiple locations include at least 50 locations and the multiple independent operators include at least 20 independent operators.

8. The method of claim 1, wherein the smoothing function is applied by a derivative filter.

9. The method of claim 1, wherein applying the smoothing function removes transient oscillations that produce a rate of temperature change of 0.125 degrees Celsius per minute or greater.

10. The method of claim 1, wherein the time series data represents between four hours and 48 hours of chiller temperature sensor data.

11. The method of claim 1, further including automatically presenting the smoothed chiller system temperature sensor data for review by a user when presenting the system unstableness determination.

12. The method of claim 1, further including comparing average and median temperatures for periods of stable operation and reporting a severity level 1 error when the average and median temperatures vary by more than a first threshold.

13. The method of claim 1, further including comparing average and median temperatures for periods of stable operation and reporting a severity level 2 error when the average and median temperatures vary by more than a second threshold.

14. A system including one or more processors coupled to memory, the memory loaded with computer instructions to detect chiller system instability, the computer instructions, when executed on the one or more processors, implement actions comprising:

applying a smoothing function to a time series of chiller temperature sensor data and reducing transient oscillations to produce a smoothed time series of chiller temperature sensor data;

determining that the smoothed time series of chiller temperature sensor data in a predefined time window fails a stable temperature operation criteria in time intervals during which temperature readings in the smoothed time series change by more than a predetermined temperature change rate from interval to interval; and generating a notification of unstableness when the smoothed time series of chiller temperature sensor data fails the stable temperature operation criteria in more than a predetermined percentage of the time intervals over the predefined time window.

15. The system of claim 14, further implementing actions comprising:

determining the predetermined temperature change rate based on equipment located at multiple locations and operated by multiple independent operators, including:
causing configuration of the equipment to log and report temperature sensor readings;
collecting logs of the temperature sensor readings;
analyzing time series of the temperature sensor readings in instances of the equipment with chiller systems that failed and determining the predetermined temperature change rate; and
storing the predetermined temperature change rate for use in the determining of the chiller system to be unstable.

16. The system of claim 14, further implementing actions comprising:

updating the predetermined temperature change rate based on equipment located at multiple locations and operated by multiple independent operators, including:
causing configuration of the equipment to log and report temperature sensor readings;
collecting logs of the temperature sensor readings and logs of service following the notifications of the unstableness;
analyzing time series of the temperature sensor readings in instances of the equipment with chiller systems that generated the notifications and service following the notifications;
determining an update to the predetermined temperature change rate based on the analyzing; and
storing the updated predetermined temperature change rate for use in the determining of the chiller system to be unstable.

17. The system of claim 14, further implementing actions comprising:

accessing logs of the temperature sensor readings from a particular chiller system in a cloud based proactive maintenance analyzer; and performing the applying, the determining and the generating the notification from the cloud based proactive maintenance analyzer.

18. The system of claim 17, further implementing actions comprising:

filtering notifications for repeat notification and submitting the filtered notifications to a customer relations management system for tracking.

19. The system of claim 17, further implementing actions comprising:

filtering notifications for repeat notification and submitting the filtered notifications to an operator of sequencer that includes the chiller system.

20. A set of one or more non-transitory computer readable storage media collectively impressed with computer program instructions to detect chiller system instability, the computer program instructions, when executed on one or more processors, implement a method comprising:

applying a smoothing function to a time series of chiller temperature sensor data and reducing transient oscillations to produce a smoothed time series of chiller temperature sensor data;

determining that the smoothed time series of chiller temperature sensor data in a predefined time window fails a stable temperature operation criteria in time intervals during which temperature readings in the smoothed time series change by more than a predetermined temperature change rate from interval to interval; and generating a notification of unstableness when the smoothed time series of chiller temperature sensor data fails the stable temperature operation criteria in more than a predetermined percentage of the time intervals over the predefined time window.

21. The set of one or more non-transitory computer readable storage media of claim 20, wherein the smoothing function is applied by a derivative filter.

22. The set of one or more non-transitory computer readable storage media of claim 20, wherein applying the smoothing function removes transitory oscillations that produce a rate of temperature change of 0.125 degrees Celsius per minute or greater.

23. The set of one or more non-transitory computer readable storage media of claim 20, wherein the time series data represents between four hours and 48 hours of chiller temperature sensor data.

24. The set of one or more non-transitory computer readable storage media of claim 20, implementing the method further comprising:

comparing average and median temperatures for periods of stable operation and reporting a missed failure when the average and median temperatures vary by more than a first threshold.

25. The set of one or more non-transitory computer readable storage media of claim 20, implementing the method further comprising:

comparing average and median temperatures for periods of stable operation and reporting a false alert when the average and median temperatures vary by more than a second threshold.

* * * * *